United States Patent
Dagher et al.

(10) Patent No.: US 10,136,642 B2
(45) Date of Patent: Nov. 27, 2018

(54) COMPOSITION OF PERACETIC ACID AND AT LEAST ONE ORGANIC FUNGICIDE FOR THE CONTROL AND/OR THE TREATMENT OF DISEASES ASSOCIATED WITH THE PRESENCE OF PATHOGENS, AND METHOD, USE AND KIT INVOLVING SAID COMPOSITION

(71) Applicant: AGRI-NEO, INC., Toronto (CA)

(72) Inventors: Fadi Dagher, Quëbec (CA); Nicholas Dillon, Toronto (CA); Steven Kent Whitesides, Toronto (CA); Johannes Mathieu, Toronto (CA)

(73) Assignee: AGRI-NEO, INC., Toronto, ON (CA)

( * ) Notice: Subject to any disclaimer, the term of this patent is extended or adjusted under 35 U.S.C. 154(b) by 0 days.

(21) Appl. No.: 15/551,800

(22) PCT Filed: Feb. 16, 2016

(86) PCT No.: PCT/CA2016/050137
§ 371 (c)(1),
(2) Date: Aug. 17, 2017

(87) PCT Pub. No.: WO2016/131133
PCT Pub. Date: Aug. 25, 2016

(65) Prior Publication Data
US 2018/0049434 A1 Feb. 22, 2018

Related U.S. Application Data

(60) Provisional application No. 62/118,249, filed on Feb. 19, 2015.

(51) Int. Cl.
*A01N 37/16* (2006.01)
*A01N 43/54* (2006.01)

(52) U.S. Cl.
CPC ............. *A01N 37/16* (2013.01); *A01N 43/54* (2013.01)

(58) Field of Classification Search
None
See application file for complete search history.

(56) References Cited

U.S. PATENT DOCUMENTS

| | | | |
|---|---|---|---|
| 2,512,640 A | 6/1950 | Greenspan et al. | |
| 5,168,655 A | 12/1992 | Davidson et al. | |
| 5,494,588 A * | 2/1996 | LaZonby | C02F 1/50 210/755 |
| 5,607,856 A | 3/1997 | Moon et al. | |
| 5,614,203 A | 3/1997 | Dezur et al. | |
| 5,658,467 A * | 8/1997 | LaZonby | A01N 37/16 210/754 |
| 5,718,910 A | 2/1998 | Oakes et al. | |
| 5,723,406 A | 3/1998 | Larose et al. | |
| 5,733,474 A | 3/1998 | Kagermeier et al. | |
| 5,785,867 A * | 7/1998 | LaZonby | A01N 37/16 210/759 |
| 5,965,033 A | 10/1999 | Huss et al. | |
| 5,980,758 A * | 11/1999 | LaZonby | C02F 1/50 210/754 |
| 6,024,986 A | 2/2000 | Hei | |
| 6,096,226 A | 8/2000 | Fuchs et al. | |
| 6,165,483 A | 12/2000 | Hei et al. | |
| 6,238,685 B1 | 5/2001 | Hei et al. | |
| 6,455,075 B1 | 9/2002 | Larose | |
| 6,514,556 B2 | 2/2003 | Hilgren et al. | |
| 6,582,961 B1 | 6/2003 | Moon et al. | |
| 6,627,593 B2 | 9/2003 | Hei et al. | |
| 6,627,657 B1 | 9/2003 | Hilgren et al. | |
| 6,635,286 B2 | 10/2003 | Hei et al. | |
| 6,797,302 B1 | 9/2004 | Ben Yehuda et al. | |
| 6,827,768 B2 | 12/2004 | Carnes et al. | |
| 6,946,155 B2 | 9/2005 | Ben Yehuda et al. | |
| 6,962,714 B2 | 11/2005 | Hei et al. | |
| 6,982,697 B2 | 1/2006 | Wilson et al. | |

(Continued)

FOREIGN PATENT DOCUMENTS

| CA | 1288334 C | 9/1991 |
|---|---|---|
| CA | 2056503 A1 | 5/1992 |

(Continued)

OTHER PUBLICATIONS

Weissinger et al., "Comparison of Aqueous chemical Treatments to Eliminate *Salmonella* on Alfalfa Seeds", Journal of Food Protection, 2000, vol. 63, No. 11, pp. 1475-1482.
Smith et al., "Microbial Synergy via an Ethanol-Triggered Pathway", Molecular and Cellular Biology, May 2004, vol. 24, No. 9, pp. 3874-3884.
Pao et al., "Utilizing Acidic Sprays for Eliminating *Salmonella enterica* on Raw Almonds", Journal of Food Science, 2006, vol. 71, No. 1, pp. M14-M19.
Bucholz et al., "Reduction of *Salmonella* on alfalfa seeds using peroxyacetic acid and a commercial seed washer is as effective as treatment with 20 000 ppm of Ca(OCl)2", Letters in Applied Microbiology, 2010, vol. 51, pp. 462-468.
Mena et al., "Influence of Ethanol on Probiotic and Culture Bacteria *Lactobacillus bulgaricus* and *Streptococcus thermophilus* within a Therapeutic Product", Journal of Medical Microbiology, 2012, vol. 2, pp. 70-76.
Beuchat et al., "Efficacy of Sanitizers in Reducing *Salmonella* on Pecan Nutmeats during Craking and Shelling", Journal of Food Protection, 2013, vol. 76, No. 5, pp. 770-778.

(Continued)

*Primary Examiner* — Brian J Davis
(74) *Attorney, Agent, or Firm* — Dority & Manning, P.A.

(57) ABSTRACT

A composition of peracetic acid and at least one organic fungicide, a method and a use involving said composition are described. The composition is for the control and/or treatment of diseases associated with the presence of pathogens, more particularly in and on the tissues of a growing plant. The composition may be a powdered composition comprising the organic fungicide(s) and a peracetic acid precursor system, which once admixed with water, may be applied to the tissues of the plant to be treated. Preferably, the peracetic acid precursor system may comprise hydrogen peroxide or a hydrogen peroxide precursor and an acetylating agent. Also described is a kit for preparing an aqueous solution of the described composition, for use in controlling pathogens on a plant tissue of a growing plant.

26 Claims, 1 Drawing Sheet

(56) References Cited

U.S. PATENT DOCUMENTS

| | | |
|---|---|---|
| 7,005,549 B2 | 2/2006 | Hobson et al. |
| 7,052,911 B2 | 5/2006 | Moon et al. |
| 7,147,872 B2 | 12/2006 | Ben-Yehuda et al. |
| 7,291,276 B1 | 11/2007 | Zahn |
| 7,307,191 B2 | 12/2007 | Hobson et al. |
| 7,326,824 B2 | 2/2008 | Campbell et al. |
| 7,615,187 B2 | 11/2009 | Helton et al. |
| 7,622,606 B2 | 11/2009 | Smith et al. |
| 7,691,630 B2 | 4/2010 | Moon et al. |
| 7,816,555 B2 | 10/2010 | Smith et al. |
| 7,832,360 B2 | 11/2010 | Hilgren et al. |
| 8,062,676 B2 | 11/2011 | Besendorfer |
| 8,246,758 B2 | 8/2012 | Man et al. |
| 2003/0114310 A1 | 6/2003 | Silverman et al. |
| 2003/0206964 A1 | 11/2003 | Larose |
| 2003/0207014 A1 | 11/2003 | Larose et al. |
| 2003/0228733 A1 | 12/2003 | Itoh et al. |
| 2003/0235623 A1 | 12/2003 | Van Oosterom |
| 2006/0029631 A1 | 2/2006 | Larose |
| 2006/0258535 A1 | 11/2006 | Larose |
| 2007/0197388 A1 | 8/2007 | Vunk et al. |
| 2008/0139435 A1 | 6/2008 | MacGregor |
| 2008/0214425 A1 | 9/2008 | Lant et al. |
| 2009/0004167 A1 | 1/2009 | Boulos et al. |
| 2009/0305888 A1 | 12/2009 | Li et al. |
| 2009/0312292 A1 | 12/2009 | Rovison et al. |
| 2010/0092574 A1 | 4/2010 | Sweeny |
| 2010/0160449 A1 | 6/2010 | Rovison, Jr. et al. |
| 2013/0259957 A1 | 10/2013 | Dagher et al. |

FOREIGN PATENT DOCUMENTS

| | | |
|---|---|---|
| CA | 2207890 A1 | 6/1996 |
| CA | 2338718 A1 | 2/2000 |
| CA | 2353645 A1 | 6/2000 |
| CA | 2371328 A1 | 1/2001 |
| CA | 2569025 A1 | 6/2008 |
| CA | 2692202 A1 | 3/2009 |
| CA | 2814794 A1 | 4/2012 |
| CN | 1543794 A | 11/2004 |
| EP | 0242990 A2 | 10/1987 |
| EP | 0648418 A1 | 4/1995 |
| EP | 0720814 A1 | 7/1996 |
| EP | 0967175 A1 | 12/1999 |
| EP | 0968188 A1 | 1/2000 |
| FR | 2728171 A1 | 6/1996 |
| GB | 2169308 A | 7/1986 |
| GB | 2268879 A | 1/1994 |
| GB | 2355198 A | 4/2001 |
| JP | 4436659 B2 | 3/2010 |
| WO | 1992019287 A1 | 11/1992 |
| WO | 1995002330 A1 | 1/1995 |
| WO | 2001083664 A1 | 11/2001 |
| WO | 2007092180 A2 | 8/2007 |
| WO | 2009027857 A1 | 3/2009 |
| WO | 2010006233 A2 | 1/2010 |
| WO | 2012037294 A2 | 3/2012 |
| WO | 2012051699 A1 | 4/2012 |
| WO | 2015039225 A1 | 3/2015 |

OTHER PUBLICATIONS

Guo et al., "Inhibitory Mechanisms of Two Silicon Compounds on Mildew Powder of Melon", Scientia Agriultura Sinica, 2005, vol. 38, No. 3, pp. 576-581.

Greenspan et al., "Analysis of Aliphatic per Acids", Analytical Chemistry, Nov. 1948, vol. 20, No. 11, pp. 1061-1063.

Fungicide Resistance Action Committee (FRAC), "Mode of Action of Fungicides", 2012, www.frac.info, 1 page.

Jian Feng Ma, "Role of Silicon in Enhancing the Resistance of Plants to Biotic and Abiotic Stresses", Soil Sci. Plant Nutr., Mini-Review Paper, 2004, vol. 50, No. 1, pp. 11-18.

Phillips McDougall—AgriService, "Products Section—2009 Market", Copyright 2010, pp. 1-310.

Martin Williams, "Resistance management bravo-quadris AzoxyPotato", Syngenta Crop Protection, Inc., Copyright 2003, Greensboro, NC, www.syngentacropprotection.com, 2 pages.

PCT International Search Report for PCT/CA2016/050137 dated Apr. 6, 2016.

PCT Written Opinion of the ISR for PCT/CA2016/050137 dated Apr. 27, 2016.

* cited by examiner

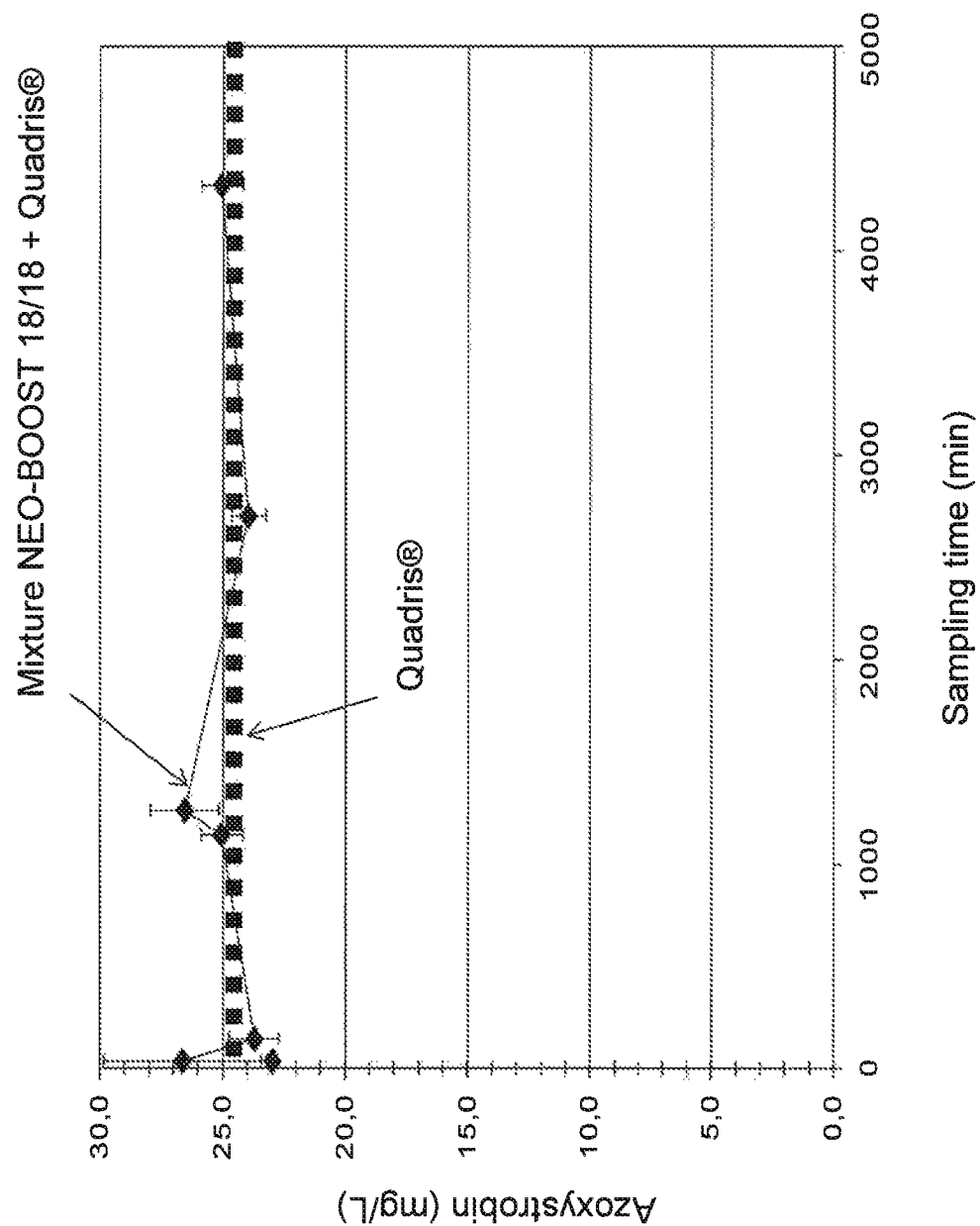

COMPOSITION OF PERACETIC ACID AND AT LEAST ONE ORGANIC FUNGICIDE FOR THE CONTROL AND/OR THE TREATMENT OF DISEASES ASSOCIATED WITH THE PRESENCE OF PATHOGENS, AND METHOD, USE AND KIT INVOLVING SAID COMPOSITION

TECHNICAL FIELD

The technical field relates to a composition of peracetic acid and at least one organic fungicide for the control and/or the treatment of diseases associated with the presence of pathogens. Uses and methods involving said composition, and a kit for the preparation of said composition are also described.

The composition may be a water soluble mixture or composition (especially a powdered composition) comprising the organic fungicide(s) and a peracetic acid precursor system, which once admixed with water, allow the control of pathogens in and on the tissues of a growing plant.

TECHNICAL BACKGROUND

Plant pathogens have a long history in developing resistance against single-site organic fungicides. Once these fungicides are introduced, mutant pathogens resistant to these single-site fungicides will emerge.

The fungicide resistance action committee (FRAC) has recommended several practices to try to avoid the development of fungicide resistance. One method is to avoid using products in isolation, but rather as mixtures with another fungicide having a different mode of action.

As per Applicant's published international patent application WO 2012/051699, a solution of the oxidizer peracetic acid, generated in situ, in combination with a plant defence enhancer demonstrated excellent anti-bactericidal and anti-fungal properties. More particularly, a synergy was evidenced when peracetic acid and at least one plant defense enhancer were used in combination for the control of pathogens in and onto growing plants. Furthermore, it was shown that the peracetic acid generated in situ is not phytoxic to plant tissues, has a wide-spectrum activity, a multi-site target mode of and can be incorporated safely with other chemicals such as potassium silicate enhancers and surfactants.

However, it is known in the field that the usual addition of oxidizers is not recommended since these oxidizing compounds have limitations and restrictions for transportation and they are highly corrosive and reactive, and they cannot be incorporated and formulated efficiently with organic fungicides.

Surprisingly, the Applicant has discovered that when using a combination of peracetic acid and at least one organic fungicide as active products, it is possible not to damage both actives while obtaining a good activity. Hence, they were able to provide a fungicide composition which can be used for resistance management applications.

Other objects, advantages and features of the technology will become more apparent upon reading of the following non-restrictive description of embodiments thereof, with reference to the accompanying drawings.

BRIEF DESCRIPTION OF THE FIGURE

The FIGURE is a diagram showing the compatibility of the peracetic acid composition NEO-BOOST™ 18/18 with the fungicide azoxystrobin in the form of Quadris®.

DETAILED DESCRIPTION

According to one aspect, there is provided a composition of peracetic acid and at least one organic fungicide for the control and/or the treatment of diseases associated with the presence of pathogens.

The expressions "to control" or "controlling" used in the present description, mean that the composition, when applied to a plant tissue of a growing plant which is affected with pathogens, is able to limit or enhance the pathogens growth, colonization and/or proliferation. In some embodiments, the composition is able to kill the pathogens thereby avoiding their colonization and/or proliferation on the plant tissue. In other words, the composition is able to control, i.e. limit or stop the spread of the disease, which is caused by the pathogen. The composition also allows treating the plant disease.

According to one embodiment, there is provided a composition comprising water soluble ingredients, wherein the soluble ingredients comprise:
 (i) peracetic acid; and
 (ii) at least one organic fungicide.

According to another embodiment, there is provided a composition comprising at least the following water soluble ingredients:
 a peracetic acid precursor comprising:
  hydrogen peroxide, a hydrogen peroxide precursor or a mixture thereof,
  an acetylating agent, and
  optionally a pH adjusting agent; and
 at least one organic fungicide;
wherein said composition generates peracetic acid (PAA) upon addition of water.

According to a further embodiment, there is provided a powdered composition comprising a dry mixture of the following water soluble ingredients:
 a peracetic acid precursor comprising:
  a solid hydrogen peroxide precursor,
  an acetylating agent, and
  optionally a pH adjusting agent; and
 at least one organic fungicide;
wherein said composition generates in situ peracetic acid (PAA) upon addition of water.

In the following description, the term "composition" refers to the compositions defined above including the powdered composition. When reference is made to the powdered composition only, this will be specified.

In an optional embodiment, the at least one organic fungicide which is used in the composition, can be a fungicide having one of the following modes of action as defined by the Fungicide Resistance Action Committee (FRAC):
 Nucleic Acid Synthesis
 Mitosis and Cell Division
 Respiration
 Amino Acid and Protein Synthesis
 Signal Transduction
 Lipid Synthesis and Membrane Integrity
 Melanin Synthesis in Cell Wall
 Sterol Biosynthesis in membranes
 Cell wall Biosynthesis
 Host Plant Defence Induction, or
 Multi Site Action;
or any other known organic fungicide having unknown Mode of Action or being not classified.

The "modes of action" as defined herein, are those defined by the Fungicide Resistance Action Committee (FRAC).

The FRAC classification on mode of action of fungicides is well known and recognized in the field of the present technology and further information on this classification is for example available on the website of the FRAC. As any one skilled in the art would understand, except for the Host Plant Defence Induction, the "modes of action" generally refer to the cellular processes of the pathogen that the fungicides interfere with. The "modes of action" refer to cellular processes that are crucial for pathogen survival, and the role of the fungicide is to disrupt these processes.

It is also worth mentioning that the organic fungicides which can be used can be bactericides, as will be apparent in the following description.

In another optional embodiment, the at least one organic fungicide present in the composition or powdered composition can be a fungicide having a mode of action consisting of Nucleic Acid Synthesis and belonging to one of the following sub-groups:
  RNA polymerase I which are PhenylAmides (PA)-fungicides, such as
    acylalanines, such as benalaxyl, benalaxyl-M, furalaxyl, metalaxyl or metalaxyl-M,
    butyrolactones, such as ofurace, or
    oxazolidinones, such as oxadixyl;
  adenosin-deaminase which are hydroxy (2-amino)-pyrimidines, such as
    bupirimate, dimethirimol or ethirimol;
  DNA/RNA synthesis (prop.) which are heteroaromatics, such as
    hymexazole or octhilinone; or
  DNA topoisomerase type II which are carboxylic acids, such as
    oxolinic acid.

In another optional embodiment, the at least one organic fungicide can be a fungicide having a mode of action consisting of Mitosis and Cell Division and belonging to one of the following sub-groups:
  β-tubulin assembly in mitosis which are Methyl Benzimidazole Carbamates (MBC) fungicides, such as
    benzimidazoles, such as benomyl, fuberidazole, carbendazim or thiabendazole, or
    thiophanates, such as thiophanate or thiophanate-methyl;
  β-tubulin assembly in mitosis which are N-phenyl carbamate, such as
    diethofencarb;
  β-tubulin assembly in mithosis which are benzamides or thiazole carboxamides, such as
    toluamide, such as zoxamide, or
    ethylamino-thiazole carboxamide, such as ethaboxam;
  cell division (prop.) which are phenylureas, such as penxycuron; or
  delocalisation of spectrin-like proteins which are benzamides, such as
    pyridinylmethyl-benzamide, such as fluopicolide.

In another optional embodiment, the at least one organic fungicide can be a fungicide having a mode of action consisting of Respiration and belonging to one of the following sub-groups:
  inhibition of complex II: succinate-dehydrogenase which are Succinate DeHydrogenase Inhibitors (SDHI), such as
    pyrazole-4-carboxamides, such as fluxapyroxad, penflufen, furametpyr, penthiopyrad, bixafen, isopyrazam, sedaxane or benzovindiflupyr,
    tiazole carboxamides, such as thifluzamide,
    phenyl-oxo-ethyl thiophene amide, such as isofetamid,
    pyridinyl-ethyl benzamides, such as fluopyram,
    phenyl benzamides, such as flutolanil, mepronil and benodanil,
    pyridine carboxamides, such as boscalid,
    oxathiin carboxamide, such as carboxin and oxycarboxin, or
    furan carboxamides, such as fenfuram;
  inhibition of complex I NADH Oxido-reductase which are pyrimidinamines pyrazole-MET1, such as
    pyrimidinamine, such as diflumetorim, or
    pyrazole-5-carboxamide, such as tolfenpyrad;
  inhibition of complex III cytochrome bc1 (ubiquinone reductase) at Qi site which are Quinone Inside Inhibitors QiI fungicides, such as
    cyano-imidazole, such as cyazofamid, or
    sulfamoyl-triazole, such as amisulbrom;
  inhibition of complex III cytochrome bc1 (ubiquinone reductase) at Qx which are Quinone x Inhibitor QxI-fungicide, such as
    ametoctradin;
  inhibitors of oxidative phosphorylation ATP synthase which are organo tins, such as
    fenti acetate, fentin chloride or fentin hydroxide;
  ATP production (prop.) which are thiophene carboxamindes, such as
    sithiofam;
  uncoupler of oxidative phosphorylation, such as
    2,6-dinitro-aniline, such as fluazinam, or
    dinitrophenyl crotonates, such as mepthyl dinocap or binapacryl); or
  inhibition of complex III—cytochrome bc1 (ubiquinol oxidase) at Qo site (cyt b gene) which are Quinone Outside Inhibitors QoI fungicides, such as
    methoxy-acrylates, such as azoxystrobin, coumoxystrobin, picosystrobin, flufenoxystriobin, enoxastrobin or pyraoxystrobin;
    oximino-acetamides, such as orysastrobin, dimoxystrobin, methminostrobin or fenaminstrobin;
    methoxy carbamates, such as pyraclostrobin, pyramethstrobin or triclopyricarb;
    oximino-acetates, such as kresoxim-methyl or trifloxystrobin;
    oxazolidine-diones, such as famoxadone;
    imidazolinones, such as fenamidone;
    benzy-l-carbamates, such as pyribencar; or
    dihydro-dioxazines (such as fluoxastrobin).

In another optional embodiment, the at least one organic fungicide can be a fungicide having a mode of action consisting of Amino Acid and Protein Synthesis and belonging to one of the following sub-groups:
  methionine biosynthesis (cgs gene) (prop.) which are aniline-pyrimidines (AP) fungicides, such as
    cyprodinil, mepanipyrim or pyrimethanil;
  protein synthesis which are enopyranuronic acid, such as
    blasticidin-S;
  protein synthesis which are hexopyranosyl antibiotics, such as
    kasugamycin;
  protein synthesis which are glucopyranosyl antibiotics, such as
    streptomycin; or
  protein synthesis which are tetracycline antibiotics, such as
    oxytetracycline.

In another optional embodiment, the at least one organic fungicide can be a fungicide having a mode of action consisting of Signal Transduction and belonging to one of the following sub-groups:
signal transduction which are azanaphthalenes, such as
aryloxyquinoline, such as quinoxyfen, or
quinazolinone, such as proquinazid;
osmotic signal transduction—MAP/histidine-kinase (os-2, HOG1) which are phenylpyrroles (PP)-fungicides, such as
fenpiclonil or fludioxonil; or
osmotic signal transduction—MAP/histidine-kinase (OS-1, Daf1) which are dicarboximides, such as
iprodione, chlozolinate, vinclozolin or procymidone.

In another optional embodiment, the at least one organic fungicide can be a fungicide having a mode of action consisting of Lipid Synthesis and Membrane Integrity and belonging to one of the following sub-groups:
phospholipid biosynthesis—methyltransferase which are phosphorothiolates or dithiolanes, such as
phosphorothiolates, such as pyrazophos, iprobenfos or edifenphos, or
dithiolanes, such as iso-prothiolane;
lipid peroxidation (prop.) which are aromatic hydrocarbons or heteroaromatics, such as
aromatic hydrocarbons, such as dicloran, tecnazene (TCNB), quintozene (PCNB), biphenyl, tolclofos-methyl or chloroneb, or
1,2,4-thiadiazole, such as etridiazole;
cell membrane permeability, fatty acids (prop.) which are carbamates, such as
propamocarb, iodocarb or prothiocarb; or
cell membrane disruption (prop.) which are plant extract, such as
melaleuca alternifolia, such as Tea Tree Extract.

In another optional embodiment, the at least one organic fungicide can be a fungicide having a mode of action consisting of Melanin Synthesis in Cell Wall and belonging to one of the following sub-groups:
reductase in melanin biosynthesis which are Melanin Biosysnthesis Inhibitors Reducase (MBI-R), such as
isobenzofuranone, such as fthalide,
pyrroloquinolione, such as pyroquilon, or
triazolobenzothiazole, such as tricyclazole; or
dehydratase in melanin biosynthesis which are Melanin Biosynthesis Inhibitors Dehydratase (MBI-D), such as
cyclopropane carboxamide, such as carpropamid,
carboxamide, such as diclocymet, or
propionamide, such as fenoxanil.

In another optional embodiment, the at least one organic fungicide can be a fungicide having a mode of action consisting of Sterol Biosynthesis in membranes and belonging to one of the following sub-groups:
C14-demethylase in sterol biosynthesis (erg11/cyp51) which are DeMethylation Inhibitors (DMI-fungicides) belonging to the Sterol Biosynthesis Inhibitor (SBI) Class I, such as
triazoles, such as etaconazole, azaconazole, ipconazole, fenbuconazole, tebuconazole, bitertanol, metconazole, fluquiconazole, tetreconazole, bromuconazole, myclobutanil, flusinazole, triadimefon, cyrpoconazole, penconazole, flutriafol, triadimenol, difenoconazole, propiconazole, hexaconazole, griticonazole, diniconazole, simeconazole, imibenzonazole or epoxiconazole,
triazolinthione, such as prothioconazole,
piperazines, such as triforine,
pyridines, such as pyrifenox or pyrisoxazole,
pyrimidines, such as nuarimol or fenarimol, or
imidazoles, such as imazalil, triflumizole, pefurazoate, oxpoconazole or prochloraz;
$\Delta^{14}$-reductase and $\Delta^8 \to \Delta^7$-isomerase in sterol biosynthesis (erg2, erg 24) which are amines "morpholines" belonging to the SBI Class II, such as
Morpholines, such as aldimorph, fenpropimorph, tridemorph or dodemorph,
Piperidines, such as fenpropidin or piperalin, or
spiroketal-amines, such as spiroxamine;
3-Keto reductase in C4-de-methylatin (erg 27) which are belonging to the SBI:Class III, such as
hydroxyanilides, such as fenhexamid, or
amino-pyrazolinones, such as fenpyrazamine; or
squalene epoxidase in sterol biosynthesis (erg1) which are belonging to the SBI class IV, such as
allylamines, such as terbinafineand naftifine, or
thiocarbamates, such as pyributicarb.

In another optional embodiment, the at least one organic fungicide can be a fungicide having a mode of action consisting of Cell wall Biosynthesis and belonging to one of the following sub-groups:
trehalase and inositol biosynthesis which are glucopyranosyl antibiotic, such as
validamycin;
chitin synthase which are polyoxins, such as
polyoxin B; or
cellulose synthase which are Carboxylic Acid Amides (CAA) fungicides, such as
cinnamic acid amides, such as dimethomorph, fluomorph or pyromorph,
mandelic acid amides, such as mandipropamid, or
valinamide carbamates, such as iprovalicarb, benthiavalicarb or valifenalate.

In another optional embodiment, the at least one organic fungicide can be a fungicide having a mode of action consisting of Host Plant Defence Induction and belonging to one of the following sub-groups:
salicylic pathway which are benzothiodiazole (BTH), such as
acibenzolar-S-methyl;
benzothiazole, such as
propenazole;
thiadiazole carboxamide, such as
isothianil, or
tiadinil;
polysaccharide, such as
laminarin; or
plant extract, such as *Reynoutria sachalinensis* (Giant Knotweed Extract).

In another optional embodiment, the at least one organic fungicide can be a fungicide having a mode of action consisting of Multi Site Action and belonging to one of the following sub-groups:
M4: phthalimides, such as
captan,
captafol, or
folpet;
M5: chloronitriles, such as
chlorothalonil;
M6: sulphamides, such as
dichlofluanid, or
tolylfluanid);

M7: guanidines, such as
  iminoctadine
  mixture of iminoctadine and other polyamides, or
  guazatine;
M8: triazine, such as
  anilazine;
M9: anthraquinones, such as
  dithianon,
M10: quinoxalines, such as
  chinomethionat; or
M11: maleimides, such as
  fluoroimide.

In another optional embodiment, the at least one organic fungicide can be a fungicide having a mode of action consisting of unknown Mode of Action and belonging to one of the following sub-groups:
  cyanoacetamide-oxime, such as
    cymoxanil;
  ethyl-phosphonates, such as
    fosetyl-al;
  phthalamic acid, such as
    teclofthalam
  cyano-methylene thiazolidine, such as
    flutianil;
  pyrimidinone-hydrazole, such as
    ferimzone;
  benzotriazine, such as
    triazoxide;
  benzene-sulfonamide, such as
    flusulfamide;
  pyridazinones, such as
    diclomezine;
  thiodarbametes, such as
    methasulfocarb;
  guanidines, such as
    dodine; or
  arylphenylketones, such as
    metrafenone or pyriofenone.

In another optional embodiment, the at least one organic fungicide can be a fungicide having a not classified Mode of Action and belonging to one of the following sub-groups:
  organic oils, or
  material of biological origin.

In another optional embodiment, the at least one organic fungicide can be an antibiotic pesticide, preferably streptomycin or oxytetracycline.

In another optional embodiment, the at least one organic fungicide can be a strobilurin, preferably pyraclostrobin, azoxystrobin or trifloxystrobin.

In another optional embodiment, the at least one organic fungicide can be a triazole, preferably triflumizole, propiconazole, or difenoconozole.

In another optional embodiment, the at least one organic fungicide can be a carbamate, chlorothalonil, captan, fenhexamide, penthiopyrad, boscalid, quinoxyfin, myclobutanil, mefenoxam, pyrimethanil, cyprodinil, fludioxonil, thiram, thiophanatemethyl, or cyflufenamid.

In another optional embodiment, the at least one organic fungicide can be the product known under the trademark Quadris® which comprises methyl (E)-2-{2-[6-(2-cyanophenoxy) pyrimidin-4-yloxy]phenyl}-3-methoxyacrylate (Azoxystrobin) in an agriculturally acceptable carrier.

In another optional embodiment, the powdered composition defined herein can further comprise at least one systemic acquired resistance (SAR) inducer.

In another optional embodiment the SAR inducer can be:
  at least one pesticide such as a water soluble silicate salt,
  at least one biopesticide such as a water soluble silicate salt,
  silica/silicate,
  DL-α-amino-n-butyric acid (AABA),
  DL-β-amino-n-butyric acid (BABA),
  γ-amino-n-butyric acid (GABA),
  p-aminobenzoic acid (PABA),
  riboflavin,
  salicylic acid (SA),
  Harpin protein (messenger),
  extract of *Reynoutria sachalinensis* (giant knotweed) such as the product
  Regalia®, or
  chitosan such as the product Elexa™.

In another optional embodiment, the SAR inducer can be potassium silicate, sodium silicate, sodium metasilicate, or any mixture thereof, preferably potassium silicate.

In another optional embodiment, the powdered composition defined herein can further comprise a sequestering agent.

In an optional embodiment, the powdered composition can comprise from 0.01 to 10% w/w of the sequestering agent.

In another optional embodiment, the powdered composition defined herein can further comprise at least one surfactant.

In an optional embodiment, the surfactant can be an anionic surfactant, a nonionic surfactant, a cationic surfactant or an amphoteric surfactant.

In an optional embodiment, the surfactant can be:
  an anionic surfactant such as a carboxylate, sulfonate, petroleum sulfonate, alkylbenzenesulfonate, naphthalene sulphonate, olefin sulphonate, alkyl sulphate, sulphated natural oil, sulphated natural fat, sulphated ester, sulphated alkanolamide, sulphated alkanolamide, ethoxylated alkylphenol or sulphated alkylphenol; or
  a non-ionic surfactant such as ethoxylated aliphatic alcohol, polyoxyethylene surfactant, carboxylic ester, polyethylene glycol ester, anhydrosorbitol ester or its ethoxylated derivarives, glycol ester of fatty acid, carboxylic amide, monoalkanolamine condensate or polyoxyethylene fatty acid amide; or
  a cationic surfactant such as a quarternary ammonium salt, amine with amide linkage, polyoxyethylene alkyl or alicyclic amine, 4-N,N,N',N'-tetrakis substituted ethylenediamine or 5,2-alkyl-1-hydroxyethyl 2-imidazoline; or
  an amphoteric surfactant such as N-coco 3-aminopropionic acid or its sodium salt, N-tallow 3-iminodipropionate or its disodium salt, N-carboxymethyl N-dimethyl N-9 octadecenyl ammonium hydroxide, or N-cocoamidethyl N-hydroxyethylglycine or its sodium salt.

In an optional embodiment, the surfactant can be an alpha olefin sulfonate, a polyglycoside, an alcohol ethoxylate or a polysorbate.

In an optional embodiment, the powdered composition can comprise less than 4% w/w of the surfactant which is a polysorbate.

In an optional embodiment, the sequestering agent present in the powdered composition defined herein can be an inorganic acid, an organic acid or a mixture of at least two acids which are inorganic acids and organic acids.

In some embodiments, the sequestering agent can be diethylene triamine pentaacetic acid (DTPA), ethylenediamine tetraacetic acid (EDTA), nitrilotriacetic acid (NTA), or a phosphonate.

The sequestering agent can also be ethylenediamine tetraacetic acid (EDTA), nitrilotriacetic Acid (NTA), diethylene triamine pentaacetic acid (DTPA), 1-hydroxyethane(1,1-diylbiphosphonic acid) (HEDP), nitrilotris (methylenephosphonic acid) (NTMP), diethylene triamine pentakis(methylenephosphonic acid) (DTPMP), 1,2-diaminoethanetetrakis (methylenephosphonic acid) (EDTMP), sodium salt of 1,2-diaminoethane tetrakis(methylenephosphonic acid), potassium salt of 1,2-diaminoethane tetrakis (methylenephosphonic acid), ammonium salt of 1,2-diaminoethane tetrakis(methylenephosphonic acid), amino trimethylene phosphonic acid (ATMP), ethylene diamine tetra (methylene phosphonic acid) (EDTMPA Solid), phosphonobutane tricarboxylic acid (PBTCA), polyhydric alcohol phosphate ester (PAPE), 2-hydroxyphosphonocarboxylic acid (HPAA), hexamethylenediamine tetra(methylenephosphonic acid) (HMDTMPA), or any mixture thereof.

The sequestering agent can further be ethylenediaminetetraacetic acid (EDTA), nitrilotriacetic acid (NTA), a phosphonate, citric acid, phosphoric acid, sulfuric acid, dipicolinic acid, sulfonic acid or boric acid.

In another embodiment, the sequestering agent can be ethylenediamine tetraacetic acid (EDTA), nitrilotriacetic acid (NTA), or a phosphonate.

In an optional embodiment, the acetylating agent, which is present in the powdered composition defined herein, can be an organic acid. For example, it can be an organic acid containing at least one acyl group which is susceptible to perhydrolysis.

In some embodiments, the acetylating agent can be a N-acyl compound or a O-acyl compound containing an acyl radical R—CO— wherein R is an aliphatic group having from 5 to 18 carbon atoms, or an alkylaryl group having from 11 to 24 carbon atoms, with 5 to 18 carbon atoms in the alkyl chain. Preferably, R is an aliphatic group having from 5 to 12 carbon atoms.

Examples of acylating agent present in the powdered composition can be tetraacetyl glycoluril (TAGU), tetraacetylethylendiamine (TAED), diacetyldioxohexahydratriazine (DADHT), or any mixture thereof. Preferably, the acylating agent can be acetylsalicylic acid or tetraacetylethylenediamine (TAED).

In another optional embodiment, the solid hydrogen peroxide precursor present in the powdered composition defined herein can be a persalt. In embodiments, the persalt can be sodium perborate, sodium percarbonate, ammonium percarbonate, sodium peroxyhydrate, calcium peroxide, sodium peroxide, sodium perborate monohydrate, sodium perborate tetrahydrate, sodium persulfate, potassium monopersulfate, perphosphate, magnesium peroxide, zinc peroxide, urea hydrogen peroxide, perhydrate of urea, thiourea dioxide, or any mixture thereof.

In another embodiment, the solid hydrogen peroxide precursor present in the powdered composition defined herein can be a persalt which is sodium percarbonate or ammonium percarbonate. Preferably, the persalt can be sodium percarbonate.

In another optional embodiment, the pH adjusting agent, when present in the powdered composition defined herein, can be an organic acid or an inorganic acid.

In some embodiments, the pH adjusting agent can be sulfuric acid, citric acid, phosphoric acid, nitric acid, hydrochloric acid, glycolic acid, formic acid, acetic acid, hydrofluoric acid, nitrous acid, hydrocyanic acid, benzoic acid, carboxylic acid, lactic acid, acetic acid, oxalic acid, sulfamic acid, phosphorous acid, dipicolinic acid, urea.HCl, boric acid, or any mixture thereof. Preferably, the pH adjusting agent can be citric acid.

According to another aspect, there is provided a method for controlling pathogens on a plant tissue of a growing plant having roots and leaves. The method comprises treating the growing plant with an aqueous solution obtained by admixing the composition or powdered composition as defined herein with water, the aqueous solution comprising peracetic acid at a concentration and a pH, which are not harmful for the plant tissue.

According to another aspect, there is provided the use of the composition as defined herein, for preparing an aqueous solution comprising peracetic acid at a concentration and a pH not harmful for a plant, for the treatment of a plant tissue of a growing plant in order to control pathogens thereon.

In one optional embodiment, the method or the use defined herein is for controlling pathogens, which can be viruses, bacteria, fungus, yeasts or molds.

In the method or the use defined herein, the aqueous solution can comprise between about 20 ppm to about 2000 ppm of peracetic acid (PAA) and the pH is 9.5±2.0. In another embodiment, the aqueous solution can comprise between about 20 ppm to about 2000 ppm of peracetic acid (PAA) and the pH is 9.5±1.5. In a further embodiment, the aqueous solution can comprise between about 20 ppm to about 2000 ppm of peracetic acid (PAA) and the pH is 9.5±1.0.

The term "about", as used before any numerical value in the present description, means within an acceptable error range for the particular value as determined by one of ordinary skill in the art. This error range may depend in part on how the value is measured or determined, i.e. the limitations of the measurement system. It is commonly accepted that a 10% precision measure is acceptable and encompasses the term "about".

In another optional embodiment, the aqueous solution can sprayed onto the leaves of the growing plant, or a substrate comprising roots of the growing plant.

In an optional embodiment, the growing plant can be a plant producing fruits, nuts, cereals, vegetables or flowers. For example, the growing plant can be a plant producing a fruit which is an apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive or lime.

In another optional embodiment, the growing plant can be a plant producing a vegetable, which is an artichoke, bean, beetroot, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip or peanut.

In another optional embodiment, the growing plant can be a plant producing a cereal. The cereal can be, for example, amaranth, breadnut, barley, buckwheat, canola, corn, fonio, kamut, millet, oats, quinoa, cattail, chia, flax, kañiwa, pitseed goosefoot, wattleseed, rice, rye, sorghum, spelt, teff, triticale, wheat, or colza.

In another optional embodiment, the growing plant can be a plant producing a nut, which is an almond, beechnut, Brazil nut, butternut, cashew, chestnut, chinquapin, filbert, hickory nut, macadamia nut, pecan, walnut or pistachio.

In another optional embodiment, the growing plant can be turf grass or long grass.

In another optional embodiment, the growing plant can be a rice crop.

Still in another optional embodiment, the growing plant can have at least a plant tissue that is a leaf, a stem, a flower, a fruit, a tuber, a rhizome, a corm, a root or a combination thereof.

In another optional embodiment, the treatment can be repeated according to a predetermined schedule.

In another optional embodiment, the aqueous solution obtained from the herein disclosed composition can comprise about 100 ppm, or about 200 ppm, or about 300 ppm, or about 400 ppm or about 500 ppm of peracetic acid (PAA).

According to another aspect, there is provided a kit for preparing an aqueous solution for use in controlling pathogens on a plant tissue of a growing plant, the kit comprising the composition defined herein, and a user manual or instructions.

In an optional embodiment, the kit is for preparing an aqueous solution for use in controlling pathogens such as viruses, bacteria, fungus, yeasts or molds.

In another optional embodiment, the method, the use or the kit defined herein is for the control of the following pathogens:

*Bremia lactucae; Peronospora destructor, Peronospora hyoscyami; Peronospora tabacina; Peronospora viciae; Phytophthora cactorum; Phytophthora capsici; cinnamomi; Phytophthora erythroseptica; Phytophthora infestans; Phytophthora megasperma* fsp. *glycinea; Phytophthora megasperma* f.sp. *medicaginis; Phytophthora melonis; Phytophthora nicotianae; Phytophthora sojae; Plasmopara halstedii; Plasmopara viticola; Pseudoperonospora cubensis; Pythium* spp.; *Ascochyta* byj; *Ascochyta* spp.; *Aspergillus nidulans; Botryodiplodia theobromae; Botrytis allii; Botrytis cinerea; Botrytis elliptica; Botrytis squamosa; Botrytis tulipae; Cercospora* spp. such as *Cercospora apii* or *Cercospora beticola; Cercosporidium personatum; Cladosporium carpophilum; Colletotrichum* spp. such as *Colletotrichum gloeosporioides* or *Colletotrichum graminicola; Corynespora cassiicola; Cryptocline cyclaminis; Cylindrocladium scoparium; Didymella bryoniae; Didymella lycopersici; Drechslera oryzae; Elsinoë fawcetti; Elsinoë veneta; Erysiphe* spp. such as *Erysiphe graminis* fsp. *hordei* or *Erysiphe necator, Fulvia fulva; Cladosporium fulvum; Fusarium culmorum; Fusarium graminearum; Fusarium nivale; Fusarium oxysporum* spp.; *Fusarium roseum; Fusarium roseum* var. *sambucinum; Fusarium solani* f. sp. *pisi; Fusarium sulphureum; Fusicladium effusum; Gibberella fujikuroi; Gloeosporium* spp.; *Glomerella acutata; Guignardia citricarpa; Helminthosporium solani; Leveillula taurica; Monilinia* spp; *Mycosphaerella* spp. such as *Mycosphaerella graminicola* or *Mycosphaerella fijiensis; Neofabraea* spp.; *Oidiopsis taurica; Oidium begonia; Penicillium* spp.; *Pestalotiopsis longiseta; Pezicula alba; Phoma* spp.; *Podosphaera leucotricha; Rhyncosporium secalis; Rhizoctonia solani; Sclerotinia fructicola; Sclerotinia homeocarpa; Sclerotinia sclerotorium; Sclerotium* spp.; *Septoria* spp. such as *Septoria apiicola; Sphaerotheca* spp. such as *Sphaerotheca fuliginea* or *Sphaerotheca aphanis* var. *aphanis; Sporobolomyces roseus; Stagonospora curtisii; Tapesia* spp.; *Trichoderma harzianum; Uncinula necator, Venturia* spp. such as *Venturia inaequalis; Verticillium* spp.; *Podosphaera xanthii; Ustilago* spp. such as *Ustilago hordei, Ustilago maydis* or *Ustilago avenae; Alternaria* spp. such as *Alternaria alternate* or *Alternaria brassicicola; Pyrenophora teres; Pyrenophora tritici-repentis; Pyricularia oryzae; Rhynchosporium secalis; Stemphylium vesicarium; Erwinia amylovora; Erwinia caratovora; Pseudomonas syringae* pv. Tomato; *Pseudomonas syringae* pv. *Syringae; Blumeria graminis; Blumeria graminis* fsp. *tritici; Botryotinia fuckeliana; Blumeriella jaapii; Cladosporium caryigenum; Fusarium asiaticum; Mycovellosiella nattrassii; Puccinia graminis* spp. such as *Puccinia striiformis* or *Puccinia triticina; Magnapoorthe oryzae*; or *Melampsora* spp.

In another optional embodiment, the method, the use or the kit defined herein is for the control of:

Downy mildew (*Bremia lactucae*) on lettuce; Downy mildew (*Peronospora destructor*) on onions; Blue mold (*Peronospora hyoscyami*) on tobacco; Blue mold (*Peronospora tabacina*) on tobacco; Downy mildew (*Peronospora viciae*) on pea; Crown rot/leather rot (*Phytophthora cactorum*) on strawberry; Stem rot (*Phytophthora capsid*) on Lima bean pods; Root rot (*Phytophthora cinnamomi*) on avocado; Pink rot (*Phytophthora erythroseptica*) on potato; Late blight (*Phytophthora infestans*) on potato; *Phytophthora megasperma* fsp. glycinea on soybean; Root rot (*Phytophthora megasperma* fsp. *medicaginis*) on lucerne; Foot rot (*Phytophthora melonis*) on cucurbits; Root rot (*Phytophthora nicotianae*) on ornamentals; Stem/root rot (*Phytophthora sojae*, synonym *P. megasperma*) on soybean; Downy mildew (*Plasmopara halstedii*) on sunflower; Downy mildew (*Plasmopara viticola*) on grapevine; Downy mildew (*Pseudoperonospora cubensis*) on cucumber; Damping off/root rot (*Pythium* spp.) on ornamentals, carrot or potato; Powdery mildew (*Erysiphe graminis* fsp. horde') on barley; Powdery mildew (*Sphaerotheca fuliginea*) on cucurbits; Alternaria rot (*Alternaria alternate*) on citrus; Ascochyta blight (*Ascochyta* byj) on vegetables; Leaf spot (*Ascochyta* spp) on pea; Bearings rot (*Aspergillus nidulans*) on banana; Botryodiplodia rot (*Botryodiplodia theobromae*) on mango fruits; Neck rot (*Botrytis allii*) on onion; Grey mold (*Botrytis cinerea*) on cyclamen; Chocolate spot (*Botrytis cinerea*) on beans; Grey rot (*Botrytis cinerea*) on grapes/vines; Grey mould (*Botrytis cinerea*) on lisianthus; Grey rot (*Botrytis elliptica*) on lily; Leaf blight (*Botrytis squamosa*) on alliacea; Fire blight (*Botrytis tulipae*) on tulip; Early blight (*Cercospora apii*) on celery; Leaf spot (*Cercospora* spp.) on peanut, sugar beet or banana; Late leaf spot (*Cercosporidium personatum*) on peanut; Scab (*Cladosporium carpophilum*) on peach or nectarine; Anthracnose (*Colletotrichum* spp.) on bean or fruit trees (e.g. pome fruit or banana); Anthracnose (*Colletotrichum graminicola*) on cereals (e.g. wheat or maize); Anthracnose (*Cryptocline cyclaminis*) on cyclamen; Stem canker (*Cylindrocladium scoparium*) on *Eucalyptus Callistemon* sp. or *Pistacia lentiscus*; Gummy stem blight (*Didymella bryoniae*) on cucurbits; Stem rot (*Didymella lycopersici*) on tomato; Brown spot (*Drechslera oryzae*) on rice; Scab (*Elsinoe fawcetti*) on citrus; Anthracnose (*Elsinoe veneta*) on raspberry; Powdery mildew (*Erysiphe* spp.) on cucurbits, cereals, cowpeas or lily; Leaf mold (*Fulvia fulva* and *Cladosporium fulvum*) on tomato; Fusariose (*Fusarium culmorum*) on potato/pink; *Fusarium* head blight (*Fusarium graminearum*) on cereals (e.g. wheat, corn or barley); Pink snow mold (*Fusarium nivale*) on wheat; Fusariose (*Fusarium oxysporum* species) on oeillet, gladiolus, tomato, tulip or melon; Fusariose (*Fusarium roseum*) on rosa or turf; Dry rot (*Fusarium roseum* var. *sambucinum*) on potato; Fusariose (*Fusarium solani* f. sp. *pisi*) on solanaceae; Dry rot (*Fusarium sulphureum*) on potato; Scab (*Fusicladium effusum*) on pecan; Fusariose (*Gibberella fujikurol*) on rice; Fruit rot (Gloeosporium spp.) on apple; Storage rot (*Glomerella acutata*) on apple; Black spot (*Guignardia citricarpa*) on citrus; Silver scurf (*Helminthosporium solani*) on potato; Powdery mildew (*Leveillula taurica*) on tomato; Brown rot (*Monilinia* spp.) on rosa or pome fruit; Ring, greasy, black, leaf, yellow spots (*Mycosphaerella* spp.) on brassicas, citrus, banana and banana; Leaf spot (*Mycosphaerella graminicola*) on wheat; Storage rot (*Neofabraea* spp.) on apple; Powdery mildew (*Oidiopsis taurica*) on artichoke; Powdery mildew (*Oidium begonia*) on begonia; Rot, green rot, blue mold, blue, stem rot (*Penicillium* spp.) on crocus, citrus, pome fruit or pear; Gray blight (*Pestalotiopsis longiseta*) on tea; Ripe spot (*Pezicula alba*) on pome fruits; Wilt and malsecco (*Phoma* spp.) on clematis or citrus; Powdery mildew (*Podosphaera leucotricha*) on fruit trees; Leaf blotch/scald (*Rhyncosporium secalis*) on barley; Brown Rhizoctonia (*Rhizoctonia solani*) on Solanaceae; Brown rot (*Sclerotinia fructicola*) on stone fruits; Dollar spot (*Sclerotinia homeocarpa*) on grass; Sclerotiniose (*Sclerotinia sclerotorium*) on oilseed rape; Stem rot (*Sclerotium* spp.) on alliacea, potato or carrot; Leaf spot (*Septoria apiicola*) on celery; Leaf spot (*Septoria* spp.) on cereals or chrysanthemum; Leaf spot (*Septoria tritici* See) on wheat; Powdery mildew (*Sphaerotheca* spp.) on cucurbits, ornamental flowers (e.g. rosa) or peach tree; Pink yeast (*Sporobolomyces roseus*) on rosa; Leaf scorch (*Stagonospora curtisii*) on ornamental flowers; Eyespot (*Tapesia* sp.) on cereals; Green mold (*Trichoderma harzianum*) on soil or mushrooms; Powdery mildew (*Uncinula necator* also know as *Erysiphe necator*) on grapes vine; Barley covered smut (*Ustilago hordei*) on barley; Scab (*Venturia* spp.) on pome fruit; *Verticillium* and wilt (*Verticillium* spp.) on pome fruits, mushrooms or tomato; Grey mold (*Botrytis cinerea*) on grapevine; Target spot (*Corynespora cassiicola*) on tomato; Seedling damping-off (*Rhizoctonia solani*) on various vegetables or ornamentals; *Alternaria* late blight (*Alternaria alternata*) on pistachio; Grey mould (*Botrytis cinerea*) on strawberry, citrus, kiwi fruit or apple; Grey mould (*Botrytis elliptica*) on lilly; Corynespora (*Corynespora cassiicola*) on cucumber; Powdery mildew (*Podosphaera xanthic*) on melon or cucumber; Smut and loose smut (*Ustilago* sp.) on maize or barley; *Alternaria* late blight, blotch, brown spot, leaf spot, late blight (*Alternaria* sp.) on pistachio, apple, citrus, potato or apple; Net Blotch (*Pyrenophora teres*) on barley; Tan spot (*Pyrenophora tritici*-repentis) on wheat; Blast (*Pyricularia oryzae*) on rice; Sheath spot and blight (*Rhizoctonia solani*) on rice; Scald, leaf blotch (*Rhynchosporium secalis*) on barley; Powdery mildew (*Sphaerotheca aphanis* var. *aphanis*) on strawberry; Powdery mildew (*Sphaerotheca fuligenea*) on cucumber; Brown stem (*Stemphylium vesicarium*) on pears; Purple spot/sand blast (*Stemphylium vesicarium*) on asparagus; Smut (*Ustilago maydis*) on maize or teosinte; Scab (*Venturia inaequalis*) on apple; Grey mold (*Botrytis cinerea*) on Adzuki bean; Leaf spot (*fijiensis* pora *beticola*) on sugar beet; Take-all (*Cercospora beticola*) on wheat; Fire blight (*Erwinia amylovora*) on pear, apple or quince; Bacterial stalk rot (*Erwinia caratovora*) on maize; Bacterial speck (*Pseudomonas syringae* pv. Tomato) on tomato; Blossom blast or canker (*Pseudomonas syringae* pv. *Syringae*) on pear; Powdery mildew (*Blumeria graminis*) on cereals (e.g. wheat) or grapevine; Powdery mildew (*Blumeria graminis* fsp. *tritici*) on cereals (e.g. wheat) or grapevine; Powdery mildew (*Erysiphe necator*) on wheat; Leaf spot (*Alternaria brassicicola*) on brassicas; Grey mold (*Botryotinia fuckeliana*) on grapevine; Leaf spot (*Blumeriella jaapii*) on cherry; Scab (*Cladosporium caryigenum*) on pecan; Anthracnose (*Colletotrichum gloeosporioides*) on mango; Powdery mildew (*Erysiphe graminis* f.sp. *hordei*) on wheat; Fusarium head blight (*Fusarium asiaticum*) on wheat; Sigatoka (*Mycosphaerella fijiensis*) on banana; Leaf mold (*Mycovellosiella nattrassii*) on eggplant; rusts (*Puccinia graminis* sp.) on wheat; Yellow/stripe rust (*Puccinia striiformis*) on wheat; Brown rust (*Puccinia triticina*) on Wheat; Loose smut (*Ustilago avenae*) on oats; blast (*Magnapoorthe oryzae*) on cereals including wheat, rye, barley, rice or pearl millet; or rust (*Melampsora* spp.) on trees.

In a further optional embodiment, the method, the use or the kit defined herein is for the control of the following pathogens:

*Botrytis cinerea*; *Erwinia amylovora*; *Mycosphaerella graminicola*; *Colletotrichum graminicola*; *Fusarium graminearum*; *Fusarium oxysporum*; *Ustilago maydis*; *Blumeria graminis*; *Puccinia graminis* sp. such as *Puccinia striiformis* or *Puccinia triticina*; *Magnapoorthe oryzae*; *Melampsora* spp.; or *Rhizoctonia solani*.

Still in another optional embodiment, the method, the use or the kit defined herein is for the control of:

Grey mold (*Botrytis cinerea*) on cyclamen; Chocolate spot (*Botrytis cinerea*) on beans; Bunch, grey or noble rot (*Botrytis cinerea*) on grapes; Grey mold (*Botrytis cinerea*) on lisianthus; Grey mold (*Botrytis cinerea*) on fruits such as strawberry, citrus, kiwi fruit or apple; Grey mold (*Botrytis cinerea*) on bulb crops; Grey mold (*Botrytis cinerea*) on Adzuki bean; Leaf spot (*Mycosphaerella graminicola*) on wheat; Anthracnose (*Colletotrichum graminicola*) on cereals such as wheat or maize; Anthracnose (*Colletotrichum graminicola*) on *allium* such as onion, garlic or leek; Anthracnose (*Colletotrichum graminicola*) on solanaceous such as pepper, tomato, or potato; Anthracnose (*Colletotrichum graminicola*) on beans, cucurbits, lettuce, cassava, cotton, coffee, strawberry, raspberry, banana, mango, citrus, or other fruit trees; Fusarium head blight (*Fusarium graminearum*) on cereals such as wheat, corn or barley or on other grass species; Fusariose or *Fusarium* Wilt (*Fusarium oxysporum* species) on tobacco, legumes, curcubits, oeillet, gladiolus, tomato, tulip, sweet potatoes, banana or other herbaceous plants; Smut (*Ustilago maydis*) on maize; Smut (*Ustilago maydis*) on teosinte such as *Euchlena Mexicana*; Powdery mildew (*Blumeria graminis*) on cereals such as wheat or on grapevine; Powdery mildew (*Blumeria graminis*) on onions, curcubits, apples, strawberries, pears or trees; rusts (*Puccinia graminis*) on wheat; Yellow/stripe rust (*Puccinia striiformis*) on wheat; Brown rust (*Puccinia triticina*) on wheat; rice blast (Magnapoorthe *oryzae*) on rice; blast or blight disease (*Magnapoorthe oryzae*) on wheat, rye, barley or pearl millet; rust (*Melampsora* spp.) on trees; fire blight (*Erwinia amylovora*) on apple or pear; or Sheath spot or blight (*Rhizoctonia solani*) on rice.

According to another embodiment, there is provided a method for controlling pathogens including *Rhizoctonia solani*, on a plant tissue of a growing plant having roots and leaves, the plant including rice, wherein the method comprises treating the growing plant with an aqueous solution resulting from the dissolution in one liter of water of:

1 to 100 grams of a powdered composition comprising:

| | |
|---|---|
| Coated sodium percarbonate | 50% w/w; |
| Tetraacetylethylenediamine (TAED) | 20% w/w; |
| Potassium silicate | 10% w/w; |
| Citric acid | 15% w/w; |
| Ethylenediaminetetraacetic (EDTA) acid | 1% w/w; |
| BIO-TERGE ™ AS-90 | 4% w/w; | and 2 to 20 ml of Quadris® which is a solution of 250 g/L azoxystrobin;

the resulting aqueous solution comprising peracetic acid at a concentration and a pH which are not harmful for said plant tissue.

According to an optional embodiment, the powdered composition used in combination with Quadris® and having the following formulation:

| | |
|---|---|
| Coated sodium percarbonate | 50% w/w; |
| Tetraacetylethylenediamine (TAED) | 20% w/w; |
| Potassium silicate | 10% w/w; |
| Citric acid | 15% w/w; |
| Ethylenediaminetetraacetic (EDTA) acid | 1% w/w; |
| BIO-TERGE ™ AS-90 | 4% w/w; | is the product named Ato Cide® Granular approved by the US Environmental Protection Agency (EPA#88306-3).

According to another embodiment, there is provided a method for controlling pathogens including *Rhizoctonia solani*, on a plant tissue of a growing plant having roots and leaves, the plant including rice, wherein the method comprises treating the growing plant with an aqueous solution resulting from the dissolution in one liter of water of:

1 to 100 grams of powdered composition comprising:

| | |
|---|---|
| Coated sodium percarbonate | 60% w/w; |
| Tetraacetylethylenediamine (TAED) | 10% w/w; |
| Potassium silicate | 18% w/w; |
| Citric acid | 10% w/w; |
| Tween ® 22 (Polysorbate) | 2% w/w; | and
2 to 20 ml of Quadris® which is a solution of 250 g/L azoxystrobin;

the resulting aqueous solution comprising peracetic acid at a concentration and a pH which are not harmful for said plant tissue.

According to an optional embodiment, the powdered composition used in combination with Quadris® and having the following formulation:

| | |
|---|---|
| Coated sodium percarbonate | 60% w/w; |
| Tetraacetylethylenediamine (TAED) | 10% w/w; |
| Potassium silicate | 18% w/w; |
| Citric acid | 10% w/w; |
| Tween ® 22 (Polysorbate) | 2% w/w; | is the product named NEO-BOOST Organic approved by the US Environmental Protection Agency (EPA#88306-4).

According to another embodiment, there is provided a method for controlling pathogens including *Rhizoctonia solani*, on a plant tissue of a growing plant having roots and leaves, the plant including rice, wherein the method comprises treating the growing plant with an aqueous solution resulting from the dissolution in one liter of water of:

3.6 grams of a powdered composition comprising:

| | |
|---|---|
| coated sodium percarbonate | 40% w/w; |
| Tetraacetylethylenediamine (TAED) | 20% w/w |
| Ethylenediaminetetraacetic (EDTA) acid | 18% w/w; |
| potassium silicate | 18% w/w; |
| BIO-TERGE ™ AS-90 | 4% w/w; | and
2 ml of Quadris® which is a solution of 250 g/L azoxystrobin;

the resulting aqueous solution comprising peracetic acid at a concentration and a pH which are not harmful for said plant tissue.

According to another embodiment, there is provided the use of an aqueous solution resulting from the dissolution in one liter of water of:

3.6 grams of a powdered composition comprising:

| | |
|---|---|
| coated sodium percarbonate | 40% w/w; |
| Tetraacetylethylenediamine (TAED) | 20% w/w |
| Ethylenediaminetetraacetic (EDTA) acid | 18% w/w; |
| potassium silicate | 18% w/w; |
| BIO-TERGE ™ AS-90 | 4% w/w; | and
2 ml of Quadris® which is a solution of 250 g/L azoxystrobin;

the resulting aqueous solution comprising peracetic acid at a concentration and a pH which are not harmful for a plant tissue, for the control of pathogens including *Rhizoctonia solani*, on the plant tissue of a growing plant having roots and leaves, the plant including rice.

According to a further embodiment, there is provided a kit for preparing an aqueous solution for use in controlling pathogens including *Rhizoctonia solani*, on a plant tissue of a growing plant having roots and leaves, the plant including rice, the kit comprising:

a powdered composition comprising:

| | |
|---|---|
| coated sodium percarbonate | 40% w/w; |
| Tetraacetylethylenediamine (TAED) | 20% w/w |
| Ethylenediaminetetraacetic (EDTA) acid | 18% w/w; |
| potassium silicate | 18% w/w; |
| BIO-TERGE ™ AS-90 | 4% w/w; |

Quadris® which is a solution of 250 g/L azoxystrobin; and a user manual or instructions.

According to an optional embodiment, the powdered composition having the following formulation:

| | |
|---|---|
| coated sodium percarbonate | 40% w/w; |
| Tetraacetylethylenediamine (TAED) | 20% w/w |
| Ethylenediaminetetraacetic (EDTA) acid | 18% w/w; |
| potassium silicate | 18% w/w; |
| BIO-TERGE ™ AS-90 | 4% w/w; | is the product named NEO-BOOST™ 18/18.

The following examples, which further illustrate the present technology, should not be construed as further limiting.

EXAMPLES

In the following examples, the NEO-BOOST™ 18/18 formulation represents a powdered product that has the following formulation before dilution in water:

| | |
|---|---|
| Coated sodium percarbonate | 40% w/w |
| Tetraacetylethylenediamine (TAED) | 20% w/w |
| Ethylenediaminetetraacetic acid (EDTA acid) | 18% w/w |
| Potassium silicate | 18% w/w |
| BIO-TERGE ™ AS-90 | 4% w/w |
| Total: | 100% w/w. |

Example 1

Efficacy of NEO-BOOST 18/18 Formulation and Quadris® Brand Azoxystrobin in the Inhibition of Growth of *Rhizoctonia solani*, the Causative Fungal Pathogen of Rice Sheath Blight Setup Rice (*Oryza sativa*) of the variety CL111 (Clearfield® 111) was grown in the field at the Rice Research Station in Crowley, La., USA in a completely randomized block design in quadruplicate. At 67 days post seeding, plants were spray inoculated with the sheath blight pathogen *Rhizoctonia solani*, followed by treatment sprays 1 day post inoculation (dpi). Disease severity was determined at timepoint 0 and every 7 days for 5 consecutive weeks, starting 3 weeks post inoculation.

Treatment List
1. Water (untreated).
2. Quadris® at 2 mL/L in water; application rate: 12 oz/acre.
3. NEO-BOOST 18/18 at 3.6 g/L in water; application rate: 2 lb/acre;
4. NEO-BOOST 18/18 at 3.6 g/L in water+Quadris® at 2 mL/L in water; application rate: 2 lb/acre+12 oz/acre.

The product Quadris® contains azoxystrobin as active ingredient at a concentration of 250 g/L.

Results

The results are reported in Table 1 below.

TABLE 1

| % Disease Control relative to untreated | |
|---|---|
| Treatment | % Control |
| 1 | 0.0 |
| 2 | 80.6 |
| 3 | 0.0 |
| 4 | 95.3 |

Quadris®, the industry standard for the treatment of sheath blight in rice, was only partially efficacious in controlling disease, resulting in a reduction in disease severity of about 80% compared to untreated plants (computed based on disease severity at the end of the trial). This is indicative of resistance of the used *Rhizoctonia* strain against Quadris®, a well-known problem in parts of Louisiana. Azoxystrobin resistant strains are spreading outwards from the area of described resistance at a rate of approximately 12 miles per year.

NEO-BOOST 18/18 by itself was inefficient against sheath blight on rice in this trial (only 3% reduction in disease severity, not statistically significant).

Surprisingly, NEO-BOOST 18/18 in a tank mix with Quadris® achieved a reduction in disease severity significantly better than either product by itself, resulting in over 95% control of disease.

Conclusions

In this trial, NEO-BOOST 18/18, when tank mixed with Quadris®, restored the efficacy of azoxystrobin against resistant *R. solani* to levels usually observed only in conjunction with non-resistant strains of the pathogen. Furthermore, the observed efficacy of the NEO-BOOST 18/18—Quadris® tank mix far exceeded the added efficacies of the two individual components.

Example 2

Efficacy of NEO-BOOST 18/18 Formulation and Quadris® Brand Azoxystrobin in the Inhibition of Growth of *Rhizoctonia solani*, the Causative Fungal Pathogen of Rice Sheath Blight Setup Rice (*Oryza sativa*) of the variety Clearfield® 151 was grown in the field in Mowata, La., USA in a completely randomized block design in hexuplicate. Inoculation occurred naturally, with *Rhizcotonia solani* in Mowata carrying confirmed resistance to Quadris® (azoxystrobin). Pesticide treatments were applied 97 days post seeding, with some delayed until 99 post seeding because of unforeseen rain. Disease incidence and severity ratings were conducted 3 (resp. 1) day post treatment and approximately 1, 3.5, 5 and 6 weeks post application. No disease was detectable at the earliest time point.

Treatment List
1. Water (untreated).
2. Quadris® at 2 mL/L in water; application rate: 12 oz/acre.
3. NEO-BOOST 18/18 at 3.6 g/L in water; application rate: 2 lb/acre;
4. NEO-BOOST 18/18 at 3.6 g/L in water+Quadris® at 2 mL/L in water; application rate: 2 lb/acre+12 oz/acre.

Results

The results are reported in Table 2 below.

TABLE 2

| % Disease Control relative to untreated | |
|---|---|
| Treatment | % Control |
| 1 | 0.0 |
| 2 | 60.5 |
| 3 | 100.0 |
| 4 | 100.0 |

Overall disease severity was low, a common phenomenon for the trial season in the area. Reflective of the described azoxystrobin resistance in the area Quadris® (Treatment 2) was only partially efficacious in controlling disease, resulting in a reduction in disease severity of only 60% compared to untreated plants (computed based on the Area Under the Disease Progress Curve (AUDPC)). Statistically, this reduction was not significant compared to untreated.

In contrast to the trial reported in Example 1, NEO-BOOST 18/18 by itself (Treatment 3) provided excellent control of sheath blight on rice in this experiment, with complete eradication of disease (100% control). NEO-BOOST 18/18 in a tank mix with Quadris® (Treatment 4) also provided a complete control of sheath blight. The effect for both treatments incorporating NEO-BOOST 18/18 is statistically significant compared to the untreated control.

Conclusions

The complete control of the disease with the combination NEO-BOOST 18/18+Quadris® and NEO-BOOST 18/18 demonstrates that the two products are compatible and can be applied together in a single treatment.

Example 3

Efficacy of NEO-BOOST 18/18 Formulation and Quadris® Brand Azoxystrobin in the Inhibition of Growth of *Rhizoctonia solani*, the Causative Fungal Pathogen of Rice Sheath Blight Setup Rice (*Oryza sativa*) of the variety Clearfield® 111 was grown in the field in Mowata, La., USA in a completely randomized block design in hexuplicate. Inoculation occurred naturally, with Rhizcotonia *solani* in Mowata having confirmed resistance to Quadris® (azoxystrobin). Pesticide treatments were applied 104 days post seeding. Disease incidence and severity ratings were conducted at day 0 (day of the treatment) and every week for 5 weeks post treatment. No disease was detectable at the earliest two time points.

Treatment List
1. Water (untreated).
2. Quadris® at 2 mL/L in water; application rate: 12 oz/acre.
3. NEO-BOOST 18/18 at 3.6 g/L in water; application rate: 2 lb/acre;
4. NEO-BOOST 18/18 at 3.6 g/L in water+Quadris® at 2 mL/L in water; application rate: 2 lb/acre+12 oz/acre.

Results
The results are reported in Table 3 below.

TABLE 3

| % Disease Control relative to untreated | |
|---|---|
| Treatment | % Control |
| 1 | 0.0 |
| 2 | 42.3 |
| 3 | 71.0 |
| 4 | 78.1 |

Overall disease severity was low, a common phenomenon for the trial season in the area. Reflective of the described azoxystrobin resistance in the area Quadris® (Treatment 2) was only partially efficacious in controlling disease, resulting in a statistically significant reduction in disease severity of only 42% compared to untreated plants (computed based on the Area Under the Disease Progress Curve (AUDPC)).

With 71% reduction in disease, NEO-BOOST 18/18 by itself (Treatment 3) provided control of sheath blight superior to that of Quadris®.

NEO-BOOST 18/18 in a tank mix with Quadris® (Treatment 4) also provided good control of sheath blight with a 78% reduction in disease AUDPC. The effect for both treatments incorporating NEO-BOOST 18/18 is statistically significant compared to the untreated control.

Conclusions
In the context of a low level natural infection, NEO-BOOST 18/18 provided excellent control of sheath blight on rice. Because of low disease pressure, none of the tested treatments are statistically significantly different, even though numerically there is a clear increase in control from Quadris® to standalone NEO-BOOST 18/18 to a tank mix of Quadris® with NEO-BOOST 18/18. It is to be noted that Quadris® fungicide had excellent control of sheath blight few years ago in this specific area before the resistance occurred.

Example 4

Compatibility of NEO-BOOST 18/18 with Strobilurins (Used in the Simultaneous Management of Rice Fungal Sheath Blight)

Setup
NEO-BOOST 18/18 at 3.6 g/L was combined with 0.5 g/L azoxystrobin in the form of Quadris®. In addition, several controls were prepared consisting of respectively: 0.5 g/L azoxystrobin in the form of Quadris®, and NEO-BOOST 18/18 at 3.6 g/L. All of the above were then converted or rendered into a form that could be analyzed by high-performance liquid chromatography (HPLC). The HPLC column was first calibrated with the reference standard azoxystrobin and then the samples were injected into the column at predetermined intervals to see whether the Quadris® was degraded at all by the NEO-BOOST 18/18.

Results
The results are represented in the FIGURE which shows the amount of azoxystrobin (in mg/L) in the sample NEO-BOOST 18/18+Quadris® eluated from the HPLC column at different times after the preparation of the sample.

Conclusion
The chromatographic output of all the eluates for all the treatments indicated that NEO-BOOST did not degrade azoxystrobin at all. This result implies that NEO-BOOST can be safely tank mixed and co-applied with Quadris® and other strobilurins in the co-management of certain bacterial and fungal diseases respectively on rice.

It is to be noted that not only did NEO-BOOST 18/18 formulation not degrade Quadris®, but also that the presence of Quadris® had no negative effect on the activity of the peracetic acid in the NEO-BOOST formulation as shown in Table 4 below.

TABLE 4 amount of peracetic acid in solution of NEO-BOOST 18/18 + Quadris ® over time versus solution of NEO-BOOST 18/18

| Solutions | NEO-BOOST alone at 3.6 g/L | NEO-BOOST 18/18 at 3.6 g/L mixed with 0.5 g/L azoxystrobin (Quadris ®) |
|---|---|---|
| After 10 min | 360 ppm Peracetic acid | 360 ppm Peracetic acid |
| After 30 min | 400 ppm Peracetic acid | 400 ppm Peracetic acid |
| After 6 hours | 400 ppm Peracetic acid | 400 ppm Peracetic acid |
| After 24 hours | 225 ppm Peracetic acid | 225 ppm Peracetic acid |

Example 5

In Vitro Efficacy of NEO-BOOST 18/18 Mixed with Antibiotics Used in the Control and Management of *Erwinia amylovora*, the Causative Bacterium of Fire Blight in Apple and Pear Setup
Virgin Luria-Bertani agar (LBA) plates were inoculated in triplicate each with 1 mL of concentrated *Erwinia amylovora* suspension by aseptically spreading the bacteria uniformly onto the agar surfaces. A center well 1 cm in diameter was punched into the agar of each plate. Test products were added dropwise into each of these center wells until the liquid level just reached the agar surface (normally 5-7 drops were required). Plates were incubated at 25° C. for 72 hours then observed for evidence of bacterial growth inhibition.

Treatment List
1. NEO-BOOST at 3.6 g/L.
2. FireLine® [oxytetracycline hydrochloride 17% w/w] at 1.2 g/L
3. FireWall® [streptomycin sulfate 17% w/w] at 0.6 g/L
4. FireLine® at 1.2 g/L+FireWall® at 0.6 g/L
5. NEO-BOOST at 3.6 g/L+FireLine® at 1.2 g/L
6. NEO-BOOST at 3.6 g/L+FireWall® at 0.6 g/L
7. NEO-BOOST at 3.6 g/L+FireLine® at 1.2 g/L+FireWall® at 0.6 g/L 8. Water.

Results

Oxytetracycline and streptomycin, both individually and in combination, produced bacterial inhibition zones of about 3 cm or ⅓ of the diameter of the plate, and the inhibitions of *Erwinia amylovora* penetrated all the way down to the agar surface below the bacterial lawn. Standalone NEO-BOOST produced an inhibition zone equal in diameter to those caused by the antibiotics but the bacteria were not killed all the way through to the agar surface. NEO-BOOST in combination with each of the antibiotics separately resulted in inhibition zones larger than those of the antibiotics alone or NEO-BOOST alone.

Conclusion

These in vitro results would suggest a bactericidal efficacy of NEO-BOOST alone against E. *Amylovora*. These results also imply a better control of *Erwinia amylovora* when antibiotics are mixed with NEO-BOOST.

Example 6

Compatibility of NEO-BOOST with Various Agrochemicals In Vitro

Setup

At concentrations ranging from 3-4 g/L, the NEO-BOOST 18/18 formulation was combined in vitro with different agrochemicals (both active ingredients and adjuvants) to determine their compatibility with NEO-BOOST. The objective was to simulate tank mixing of the various products in a field application setting. The criterion was whether the products degraded the peracetic acid generated by the 18/18 after it was dissolved in water.

Formulations List

1. NEO-BOOST 18/18 at 3.6 g/L+Cueva® at 3 mL/L
2. NEO-BOOST 18/18 at 3.6 g/L+Cueva® at 5 mL/L
3. NEO-BOOST 18/18 at 4 g/L+Cueva® at 5 mL/L
4. NEO-BOOST 18/18 at 3.6 g/L+Cueva® at 10 mL/L
5. NEO-BOOST 18/18 at 3.6 g/L+Quadris® at 2 mL/L
6. NEO-BOOST 18/18 at 3.6 g/L+AgSorb®
7. NEO-BOOST 18/18 at 3.6 g/L+Bravo®
8. NEO-BOOST 18/18 at 3.6 g/L+Bumper®
9. NEO-BOOST 18/18 at 3.6 g/L+Cabrio®
10. NEO-BOOST 18/18 on 3.6 g/L+Coragen®
11. NEO-BOOST 18/18 at 3.6 g/L+Switch®
12. NEO-BOOST 18/18 at 3.6 g/L+Verge®
13. NEO-BOOST 18/18 at 3.6 g/L+Stratego® at 2 mL/L
14. NEO-BOOST 18/18 at 3.6 g/L+Sercadis® at 2 mL/L
15. NEO-BOOST 18/18 at 3.6 g/L+Regalia® at 2 mL/L
16. NEO-BOOST 18/18 at 3.6 g/L+Quilt® at 2 mL/L Active Product List AgSorb®: attapulgite clay
Bravo®: chlorothalonil
Bumper®: propiconazole
Cabrio®: pyraclostrobin
Coragen®: rynaxypyr
Cueva®: copper octanoate
Quadris®: azoxystrobin
Switch®: cyprodinil+fludioxinil
Verge®: flutriafol
Stratego®: prothioconazole
Sercadis®: Fluxapyroxad
Regalia®: Plant extract, Knotweed
Quilt®: Azoxystrobin and Propiconazole Results and Conclusions The tested products did not or did not significantly degrade the peracetic acid generated from NEO-BOOST 18/18 even 6 hours following tank mixing.

Cabrio® and Quadris® are strobilurins which did not decompose the peracetic acid from NEO-BOOST 18/18 to any extent. Therefore, this class of chemicals can be tank mixed with NEO-BOOST 18/18.

Stratego® (prothioconazole), Sercadis® (Fluxapyroxad) and Quilt® (Azoxystrobin and Propiconazole) fungicides did not decompose the peracetic acid from NEO-BOOST 18/18 to any extent. Therefore, this class of chemicals can be tank mixed with NEO-BOOST 18/18.

The concentration of free copper in Cueva® (copper octanoate) is below the threshold at which unbound copper degrades the peracetic acid generated from 18/18; therefore this product can be tank mixed with NEO-BOOST 18/18.

Example 7

Compatibility of NEO-BOOST Registered and NEO-BOOST Organic with Various Agrochemicals In Vitro The experiment of Example 6 was repeated with two different variations of the NEO-BOOST 18/18 formulation: NEO-BOOST Registered (also called Ato Cide®) and NEO-BOOST Organic. All formulations performed similarly to NEO-BOOST 18/18.

NEO-BOOST Registered is a product having the following formulation before dilution in water:

| | |
|---|---|
| Coated sodium percarbonate | 50% w/w; |
| TAED | 20% w/w; |
| Citric acid | 15% w/w; |
| EDTA acid | 1% w/w; |
| potassium silicate | 10% w/w; |
| BIO-TERGE ™ AS-90 | 4% w/w; |
| Total: | 100% w/w. |

NEO-BOOST Organic is a product which has the following formulation before dilution in water:

| | |
|---|---|
| Coated sodium percarbonate | 60% w/w; |
| TAED | 10% w/w; |
| Citric acid | 10% w/w; |
| potassium silicate | 18% w/w; |
| Tween ® 22 (Polysorbate) | 2% w/w; |
| Total: | 100% w/w. |

All formulations performed similarly to NEO-BOOST 18/18. Both NEO-BOOST Registered and NEO-BOOST Organic were compatible with single-site fungicides such as azoles and strobilurins.

Example 8

Compatibility of NEO-PURE™ Liquid with Single-Site Fungicides Such as Azoles and Strobilurins In Vitro Another liquid organic formulation based on pre-formed peracetic acid, called NEO-PURE™ Liquid, was formulated to study its compatibility with single-site fungicides such as azoles and strobilurins.

Formulation of NEO-PURE™ Liquid

| | |
|---|---|
| Distilled Water | 21.0% w/w |
| Acetic Acid 92% | 13.5% w/w |
| Sulphuric Acid 96% | 1.1% w/w |
| Hydrogen Peroxide 50% | 62.0% w/w |
| Citric Acid - Food grade | 0.9% w/w |
| APG 325N (Polyglycoside surfactant) | 1.5% w/w |
| TOTAL: | 100% w/w. |

The above formulation contains a minimum of 5% w/w active peracetic acid and 20% w/w hydrogen peroxide.

The results are reported in the Table 5.

TABLE 5 amount of peracetic acid in solution of NEO-PURE ™ Liquid + Quadris ® over time versus solution of NEO-PURE ™ Liquid

| Solutions | NEO-PURE ™ Liquid alone at 8 ml/L | NEO-PURE ™ Liquid at 4 ml/L mixed with 0.5 g/L azoxystrobin (Quadris ®) |
|---|---|---|
| After 10 min | 400 ppm Peracetic acid | 400 ppm Peracetic acid |
| After 30 min | 400 ppm Peracetic acid | 400 ppm Peracetic acid |
| After 6 hours | 400 ppm Peracetic acid | 400 ppm Peracetic acid |
| After 24 hours | 300 ppm Peracetic acid | 300 ppm Peracetic acid |

The results show that even liquid peracetic acid at diluted concentrations can be tank-mixed with single-site fungicides. Peracetic acid was not decomposed by the presence of azoxystrobin over time.

Example 9

Combination of Efficacy Between Ato Cide® Granular (EPA#88306-3) at 4 Lbs/Acre and Quadris® Brand Azoxystrobin in the Inhibition of Growth of *Rhizoctonia solani*, the Causative Fungal Pathogen of Rice Sheath Blight Setup Rice (*Oryza sativa*) of the variety Clearfield® 111 was grown in the field in Mowata, La., USA in a completely randomized block design small plot trial in hexuplicate. Inoculation occurred naturally, with *Rhizcotonia solani* in Mowata having confirmed resistance to Quadris® (azoxystrobin). Pesticide treatments were applied 90 days post seeding. The Ato Cide® Granular formulation (Environmental Protection Agency reference: EPA#88306-3) was used instead of the previously used NEO-BOOST 18/18 formulation to ensure comparability with the aerial trials conducted in parallel (see Example 11). Disease incidence and severity ratings were conducted at day 1 (one day after the treatment) and 1, 3 and 5 weeks post treatment. Marginal disease was detectable at the earliest time points (average across replicates less than 1 on 0-11 Horsfell Barratt scale, equivalent to 0-3% plant surface affected).

Formulation of Ato Cide® Granular

| | |
|---|---|
| Coated sodium percarbonate | 50% w/w; |
| Tetraacetylethylenediamine (TAED) | 20% w/w; |
| Potassium silicate | 10% w/w; |
| Citric acid | 15% w/w; |
| Ethylenediaminetetraacetic (EDTA) acid | 1% w/w; |
| BIO-TERGE ™ AS-90 | 4% w/w; |

Treatment List
1. Untreated Control.
2. Quadris® at 2 mL/L in water; application rate: 12 oz/acre.
3. Ato Cide® Granular at 7.2 g/L in water; application rate: 4 lb/acre;
4. Ato Cide® Granular at 7.2 g/L in water+Quadris® at 2 mL/L in water; application rate: 4 lb/acre+12 oz/acre.

Results

The results are reported in Table 6 below.

TABLE 6

% Disease Control relative to untreated

| Treatment | % Control |
|---|---|
| 1 | 0.0 |
| 2 | 10.0 |
| 3 | 30.0 |
| 4 | 36.0 |

During the 2015 trial year, sheath blight disease pressure was very high, as observed across the whole Mowata area. Reflective of the described azoxystrobin resistance in the area Quadris® (treatment 2) was almost non efficacious in controlling disease, resulting in only minor (although in this case statistically significant) reduction of disease severity by 10% compared to untreated plants (computed based on the Area Under the Disease Progress Curve (AUDPC)).

With 30% reduction in disease, Ato Cide® Granular at 4 lb/a by itself (Treatment 3) provided control of sheath blight statistically significantly superior to that of Quadris®.

Ato Cide® Granular in a tank mix with Quadris® (Treatment 4) provided even better control of sheath blight with a 36% reduction in disease AUDPC. The effect for both treatments incorporating Ato Cide Granular is statistically significant compared to both untreated control and Quadris® only.

Conclusions

In the context of this trial, conducted during the high sheath blight disease pressure 2015 season, Ato Cide® Granular provided robust control of sheath blight on rice. All treatments incorporating Ato Cide® Granular are significantly superior to both untreated controls and Quadris® only treatments; Ato Cide® Granular statistically significantly enhanced Quadris® performance when combined as a tank mix.

Example 10

Combination of Efficacy Between Ato Cide® Granular (EPA#88306-3) at 2 Lbs/Acre and Quadris® Brand Azoxystrobin in the Inhibition of Growth of *Rhizoctonia solani*, the Causative Fungal Pathogen of Rice Sheath Blight Setup Rice (*Oryza sativa*) of the variety Clearfield® 111 was grown in the field in Mowata, La., USA in randomized block design small plot trial in hexuplicates. Inoculation occurred naturally, with *Rhizcotonia solani* in Mowata having confirmed resistance to Quadris® (azoxystrobin). Pesticide treatments were applied 90 days post seeding. The Ato Cide® Granular (EPA#88306-3) was employed instead of the previously used NEO-BOOST 18/18 formulation to ensure comparability with the aerial trials conducted in parallel (see Example 11). Disease incidence and severity ratings were conducted at day −3 (3 days before the treatment) and 1, 3 and 5 weeks post treatment. Marginal disease was detectable at the earliest time point (average across individual replicates between 0 and 2 on 0-11 Horsfall-Barratt scale, equivalent to 0-6% plant surface affected).

Treatment List
1. Untreated Control
2. Quadris® at 2 mL/L in water; application rate: 12 oz/acre.
3. Ato Cide® Granular at 3.6 g/L in water; application rate: 2 lb/acre;
4. Ato Cide® Granular at 3.6 g/L in water+Quadris® at 2 mL/L in water; application rate: 2 lb/acre+12 oz/acre.

Results

The results are reported in Table 7 below.

TABLE 7

| % Disease Control relative to untreated | |
|---|---|
| Treatment | % Control |
| 1 | 0.0 |
| 2 | 11.0 |
| 3 | 19.0 |
| 4 | 24.0 |

During the 2015 trial year, sheath blight disease pressure was very high, as observed across the whole Mowata area. Reflective of the previously described azoxystrobin resistance in the area, Quadris® (Treatment 2) was almost non efficacious in controlling disease, resulting in an only minor and statistically not significant reduction of disease severity of 11% compared to untreated plants (computed based on the Area Under the Disease Progress Curve (AUDPC)).

With 19% reduction in disease, Ato Cide® Granular at 2 lb/acre by itself (treatment 3) provided control of sheath blight that, in contrast to Quadris® by itself, was statistically significantly superior to the untreated control.

Ato Cide® Granular in a tank mix with Quadris® (Treatment 4) provided even better control of sheath blight, with a 24% reduction in disease AUDPC. The effect of this treatment is statistically significantly superior compared to both untreated control and Quadris® only.

Conclusions

In the context of very high disease pressure during the 2015 season, Ato Cide® Granular provided robust control of sheath blight on rice, both as a standalone and in combination with Quadris®. All treatments incorporating Ato Cide® Granular proved superior to the untreated controls and Quadris® only treatments, and the enhancement of Quadris® performance gained by the addition of Ato Cide® Granular as a tank mix was statistically significant.

Example 11

Compatibility of a Ato Cide® Granular (EPA#88306-3) and Quadris® Brand Azoxystrobin with Application by Plane and Enhancement of Control of *Rhizoctonia solani*, the Causative Fungal Pathogen of Rice Sheath Blight, by a Combination of Ato Cide® Granular (EPA#88306-3) and Quadris®

Setup

Rice (*Oryza sativa*) of the variety Clearfield® 111 was grown in a commercial rice field in Mowata, La., USA. The field was divided into 100 by 100 foot sections (10.000 ft$^2$) to allow application by airplane, as is common practice in rice farming in the area. Inoculation occurred naturally, with *Rhizoctonia solani* in Mowata carrying confirmed resistance to Quadris® (azoxystrobin). Application from an airplane required some modifications to the previously used protocols, most importantly the preparation of a highly concentrated (4x) stock solution containing 96 g/L Ato Cide® Granular (EPA#88306-3) and 36 ml/L Quadris®. This premix was then transferred into the airplane spray tank and water added to obtain the final spray solution containing 24 g/L Ato Cide® Granular and 2 ml/L Quadris®. The Ato Cide® Granular formulation was used based on initial experiments showing it to be very compatible with Quadris® even at extremely high concentrations, and its registration status in the US that allowed to conduct this experiment as a 'non crop destruct' trial, which given the scale significantly reduced costs. Pesticide treatments were applied 89 days post seeding by plane, at application rates of 10 gallons per acre. Disease incidence and severity ratings were conducted at day −1 (one day before treatment) and 7, 14, 21, 30 and 40 days post treatment. Weak disease (2 on a modified Horsfall-Barratt Scale, equivalent to 3-6% infected leaf surface) was detectable at the earliest time point. The scale of the testplot also allowed the collection of data to assess the impact of the different treatments on yield. A 35 ft wide swath in the center of each treatment section was harvested 50 days after treatment (139 days post seeding) and yields before and after each cleaning step were determined.

Treatment List
1. Quadris® at 9 mL/L in water; application rate: 12 oz/acre.
2. Ato Cide® Granular at 24 g/L in water; application rate: 2 lb/acre
3. Ato Cide® Granular at 24 g/L+Quadris® at 2 mL/L in water; application rate: 2 lb/acre+12 oz/acre.

Results

The results are reported in Table 8 below.

TABLE 8

| % Disease Control relative to untreated | | | |
|---|---|---|---|
| Treatment | Disease Severity (0-11 HB Scale*) | % Control relative to Quadris ® | % Final Yield |
| 1 | 6 | 100 | 100 |
| 2 | 5 | 124 | 97.1 |
| 3 | 4 | 127 | 104 |

*HB Scale: Horsfall-Barratt scale

Disease severity in the Mowata area was high in 2015. Reflective of the described azoxystrobin resistance in the area, Quadris® (Treatment 1) was only partially efficacious in controlling disease. The scale of this trial, necessary to allow us to test aerial application, precluded a non-treated negative control, as the necessary yield loss compensations were cost prohibitive. However, the high endpoint disease severity in the Quadris®-only treatment (treatment 1) of 6 on the HB scale (equivalent to 50-75% infection of the leaf surface) confirms the presence of resistant *Rhizoctonia* strains, as did independent small plot trials conducted directly adjacent to this field.

With 24% higher reduction in disease AUDPC compared to Quadris®, Ato Cide® Granular by itself (Treatment 2) provided control of sheath blight superior to that of Quadris®. However, this did not result in higher yields.

Ato Cide® Granular in a tank mix with Quadris® (Treatment 3) provided even better control of sheath blight with a 27% reduction in disease symptoms. Furthermore, this also resulted in a 4% higher yield as compared to Quadris® only.

Conclusions

In the context of a high level natural infection, Ato Cide® Granular provided excellent control of sheath blight on rice, and is fully compatible with application by airplane at the necessary lower application rates and high concentration of actives (23.9 g/L Ato Cide® Granular and 9.3 ml/L Quadris®). It is worth noting that Quadris® fungicide had excellent control of sheath blight few years ago in this specific area, before azoxystrobin resistance emerged.

The above-described embodiments and examples are considered in all respect only as illustrative and not restrictive, and the present application is intended to cover any adaptations or variations thereof, as apparent to a person skilled in the art. Of course, numerous other modifications could be made to the above-described embodiments without departing from the scope of the invention, as apparent to a person skilled in the art.

The scope of the invention is therefore intended to be limited solely by the scope of the appended claims.

The invention claimed is:

1. A composition comprising water soluble ingredients comprising:

(i) peracetic acid; and (ii) at least one organic fungicide, wherein the at least one organic fungicide comprises a fungicide having a mode of action consisting of:

I) Respiration and belonging to one of the following sub-groups:

inhibition of complex II: succinate-dehydrogenase which are Succinate DeHydrogenase Inhibitors (SDHI);

inhibition of complex I NADH Oxido-reductase which are pyrimidinamines pyrazole-MET1;

inhibition of complex III cytochrome bc1 (ubiquinone reductase) at Qi site which are Quinone Inside Inhibitors QiI fungicides;

inhibition of complex III cytochrome bc1 (ubiquinone reductase) at Qx which are Quinone x Inhibitor QxI-fungicide;

inhibitors of oxidative phosphorylation ATP synthase which are organo tins;

ATP production (prop.) which are thiophene carboxamides;

uncoupler of oxidative phosphorylation;

or inhibition of complex III cytochrome bc1 (ubiquinol oxidase) at Qo site (cyt b gene) which are Quinone Outside Inhibitors QoI fungicides selected from the group consist of methoxy-acrylates, oximino-acetamides, oximino-acetates, oxazolidine-diones, imidazolinones and dihydro-dioxazines;

II) Amino Acid and Protein Synthesis and belonging to one of the following sub-groups:

methionine biosynthesis (cgs gene) (prop.) which are aniline-pyrimidines (AP) fungicides;

protein synthesis which are hexopyranosyl antibiotics;

protein synthesis which are glucopyranosyl antibiotics; or protein synthesis which are tetracycline antibiotics; or III) Sterol Biosynthesis in membranes and belonging to one of the following sub-groups:

C14-demethylase in sterol biosynthesis (erg11/cyp51) which are DeMethylation Inhibitors (DMI-fungicides) belonging to the Sterol Biosynthesis Inhibitor (SBI) Class I;

$\Delta^{14}$-reductase and $\Delta^{8}\rightarrow\Delta^{7}$-isomerase in sterol biosynthesis (erg2, erg 24) which are amines "morpholines" belonging to the SBI Class II;

3-Keto reductase in C4-de-methylatin (erg 27) which are belonging to the SBI:Class III; or squalene epoxidase in sterol biosynthesis (erg1) which are belonging to the SBI class IV.

2. The composition of claim 1, wherein the at least one organic fungicide comprises an antibiotic pesticide selected from the group consisting of hexopyranosyl antibiotics, glucopyranosyl antibiotics and tetracycline antibiotics; a strobilurin selected from the group consisting of azoxystrobin, coumoxystrobin, picoxystrobin, flufenoxystrobin, enoxastrobin, pyraoxystrobin, orysastrobin, dimoxystrobin, metonminostrobin, fenaminstrobin, kresoxim-methyl, trifloxystrobin and fluoxastrobin; or a triazole.

3. The composition of claim 1, wherein the at least one organic fungicide comprises an antibiotic pesticide, which is streptomycin or oxytetracycline.

4. The composition of claim 1, wherein the at least one organic fungicide comprises a strobilurin, which is azoxystrobin or trifloxystrobin.

5. The composition of claim 1, wherein the at least one organic fungicide comprises a triazole, which is triflumizole, propiconazole, or difenoconozole.

6. The composition of claim 1, wherein the at least one organic fungicide comprises chlorothalonil, captan, fenhexamide, penthiopyrad, boscalid, quinoxyfen, myclobutanil, mefenoxam, pyrimethanil, cyprodinil, fludioxonil, thiram, or cyflufenamid.

7. The composition of claim 1, wherein the at least one organic fungicide comprises methyl (E)-2-{2-[6-(2-cyanophenoxy)pyrimidin-4-yloxy]phenyl}-3-methoxyacrylate (Azoxystrobin) in an agriculturally acceptable carrier.

8. A composition comprising a dry mixture of the following water soluble ingredients:

a peracetic acid precursor comprising:

a solid hydrogen peroxide precursor, an acetylating agent, and optionally a pH adjusting agent; and at least one organic fungicide;

wherein said composition generates in situ peracetic acid (PAA) upon addition of water.

9. The composition of claim 8, wherein the at least one organic fungicide comprises a fungicide having a mode of action consisting of:

I) Respiration and belonging to one of the following sub-groups:

inhibition of complex II: succinate-dehydrogenase which are Succinate DeHydrogenase Inhibitors (SDHI);

inhibition of complex I NADH Oxido-reductase which are pyrimidinamines pyrazole-MET1;

inhibition of complex Ill cytochrome bc1 (ubiquinone reductase) at Qi site which are Quinone Inside Inhibitors Oil fungicides;

inhibition of complex III cytochrome bc1 (ubiquinone reductase) at Ox which arc Quinone x Inhibitor QxI-fungicide;

inhibitors of oxidative phosphorylation ATP synthase which are organo tins;

ATP production (prop.) which are thiophene carboxamindes;

uncoupler of oxidative phosphorylation; or inhibition of complex III—cytochrome bc1 (ubiquinol oxidase) at Qo site (cyt b gene) which are Quinone Outside Inhibitors QoI fungicides;

II) Amino Acid and Protein Synthesis and belonging to one of the following sub-groups:
methionine biosynthesis (cgs gene) (prop.) which are aniline-pyrimidines (AP) fungicides;
protein synthesis which are hexopyranosy antibiotics;
protein synthesis which are glucopyranosyl antibiotics; or
protein synthesis which are tetracycline antibiotics; or III) Sterol Biosynthesis in membranes and belonging to one of the following sub-groups:
C14-dernethylase in sterol biosynthesis (erg11/cyp51) which are DeMethylation Inhibitors (DMI-fungicides) belonging to the Sterol Biosynthesis Inhibitor (SBI) Class I;
$\Delta^{14}$-reductase and $\Delta^8 \to \Delta^7$-isomerase in sterol biosynthesis (erg2, erg 24) which are amities "morpholines" belonging to the SBI Class II;
3-Keto reductase in C4-de-methylatin (erg 27) which are belonging to the SBI:Class III; or
squalene epoxidase in sterol biosynthesis (erg1) which are belonging to the SBI class IV.

10. The composition of claim 8, wherein the at least one organic fungicide comprises an antibiotic pesticide, a strobilurin or a triazole.

11. The composition of claim 8, wherein the at least one organic fungicide comprises an antibiotic pesticide, which is streptomycin or oxytetracycline.

12. The composition of claim 8, wherein the at least one organic fungicide comprises a strobilurin, which is pyraclostrobin, azoxystrobin or trifloxystrobin.

13. The composition of claim 8, wherein the at least one organic fungicide comprises a triazole, which is triflumizole, propiconazole, or difenoconozole.

14. The composition of claim 8, wherein the at least one organic fungicide comprises methyl (E)-2-{2-[6-(2-cyanophenoxy)pyrimidin-4-yloxy]phenyl}-3-methoxyacrylate (Azoxystrobin) in an agriculturally acceptable carrier.

15. The composition of claim 8 which further comprises at least one systemic acquired resistance (SAR) inducer and/or a sequestering agent and/or at least one surfactant.

16. The composition of claim 15, wherein the at least one SAR inducer is:
at least one water soluble silicate salt,
silica/silicate,
DL-α-amino-n-butyric acid (AABA),
DL-β-amino-n-butyric acid (BABA),
γ-amino-n-butyric acid (GABA),
p-aminobenzoic acid (PABA),
riboflavin,
salicylic acid (SA),
Harpin protein (messenger),
extract of Reynoutria sachalinnsis (giant knotweed), or
chitosan.

17. The composition of claim 15, wherein the surfactant is
an anionic surfactant comprising a carboxylate, sulfonate, petroleum sulfonate, alkylbenzenesulfonate, naphthalene sulphonate, olefin sulphonate, alkyl sulphate, sulphated natural oil, sulphated natural fat, sulphated ester, sulphated alkanolamide, sulphated alkanolamide, ethoxylated alkylphenol or sulphated alkylphenol; or
a non-ionic surfactant comprising ethoxylated aliphatic alcohol, polyoxyethylene surfactant, carboxylic ester, polyethylene glycol ester, anhydrosorbitol ester or its ethoxylated derivarives, glycol ester of fatty acid, carboxylic amide, monoalkanolamine condensate or polyoxyethylene fatty acid amide; or
a cationic surfactant comprising a quarternary ammonium salt, amine with amide linkage, polyoxyethylene alkyl or alicyclic amine, 4-N,N,N',N'-tetrakis substituted ethylenediamine or 5,2-alkyl-1-hydroxyethyl 2-imidazoline; or
an amphoteric surfactant comprising N-coco 3-aminopropionic acid or its sodium salt, N-tallow 3-iminodipropionate or its disodium salt, N-carboxymethyl N-dimethyl N-9 octadecenyl ammonium hydroxide, or N-cocoamidethyl N-hydroxyethylglycine or its sodium salt.

18. The composition of claim 15, wherein the sequestering agent is ethylenediamine tetraacetic acid (EDTA), nitrilotriacetic acid (NTA), or a phosphonate.

19. The composition of claim 8, wherein the acylating agent is acetylsalicylic acid, tetraacetyl glycoluril (TAGU), tetraacetylethylendiamine (TAED), diacetyldioxohexahydratriazine (DADHT), or any mixture thereof.

20. The composition of claim 8, wherein the solid hydrogen peroxide precursor is sodium perborate, sodium percarbonate, ammonium percarbonate, sodium peroxyhydrate, calcium peroxide, sodium peroxide, sodium perborate monohydrate, sodium perborate tetrahydrate, sodium persulfate, potassium monopersulfate, perphosphate, magnesium peroxide, zinc peroxide, urea hydrogen peroxide, perhydrate of urea, thiourea dioxide, or any mixture thereof.

21. A method for controlling pathogens comprising viruses, bacteria, fungus, yeasts or molds on a plant tissue of a growing plant having roots and leaves, wherein the method comprises treating the growing plant with an aqueous solution obtained by admixing the composition as defined in claim 8 with water, the aqueous solution comprising peracetic acid at a concentration and a pH which are not harmful for the plant tissue.

22. The method of claim 21, wherein the aqueous solution comprises between about 20 ppm to about 2000 ppm of peracetic acid (PAA) and the pH is 9.5 ±2.0.

23. The method of claim 21, wherein the growing plant is a plant producing
a fruit which is an apple, apricot, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive or lime;
a vegetable which is an artichoke, bean, beetroot, broccoli, cabbage, carrot, cauliflower, celery, chicory, chives, cress, cucumber, kale, dill, eggplant, kohlrabi, lettuce, onion, paprika, parsnip, parsley, pea, potato, pumpkin, radish, shallot, soybean, spinach, turnip or peanut; or a plant producing a cereal.

24. A method for controlling pathogens *Rhizoctonia solani*, on a plant tissue of a growing plant having roots and leaves, wherein the method comprises treating the growing plant with an aqueous solution resulting from the dissolution in one liter of water of:
1 to 100 grams of a powdered composition comprising:

| | |
|---|---|
| coated sodium percarbonate | 50% w/w; |
| Tetraacetylethylenediamine (TAED) | 20% w/w; |
| Potassium silicate | 10% w/w; |
| Citric acid | 15% w/w; |
| Ethylenediaminetetraacetic (EDTA) acid | 1% w/w; |
| Alpha olefin sulfonate | 4% w/w; | and
2 to 20 ml of a solution of 250 g/L azoxystrobin; or
1 to 100 grams of a powdered composition comprising:

| | |
|---|---|
| coated sodium percarbonate | 60% w/w; |
| Tetraacetylethylenediamine (TAED) | 10% w/w; |
| Potassium silicate | 18% w/w; |
| Citric acid | 10% w/w; |
| (Polysorbate) | 2% w/w; | and
2 to 20 ml of a solution of 250 g/L azoxystrobin; or
3.6 grams of a powdered composition comprising:

| | |
|---|---|
| coated sodium percarbonate | 40% w/w; |
| Tetraacetylethylenediamine (TAED) | 20% w/w |
| Ethylenediaminetetraacetic (EDTA) acid | 18% w/w; |
| potassium silicate | 18% w/w; |
| Alpha olefin sulfonate | 4% w/w; | and
2 ml of a solution of 250 g/L azoxystrohin;
the resulting aqueous solution comprising peracetic acid at a concentration and a pH which are not harmful for said plant tissue.

25. The method of claim 21 for the control of the following pathogens:

*Bremia lactucae; Peronospora destructor; Peronospora hyoscyami; Peronospora tabacina; Peronospora viciae; Phytophthora cactorurn; Phytophthora capsici; cinnamomi; Phytophthora erythroseptica; Phytophthora infestans; Phytophthora megasperma* f.sp. *glycinea; Phytophthora megasperma* f.sp. *medicaginis; Phytophthora melonis; Phytophthora nicotianae; .Phytophthora sojae; Plasmopara halstedii; Plasmopara viticola; Pseudoperonospora cubensis; Pythium* spp.; *Ascochyta byj; Ascochyta* spp.; *Aspergillus nidulans; Botryodiplodia theobromae; Botrytis allii; Botrytis cinerea; Botrytis elliptica; Botrytis squamosa; Botrytis tulipae; Cercospora* spp.; *Cercosporidium personatum; Cladosporium carpophilum; Colletotrichum* spp.; *Corynespora cassilcola; Cryptocline cyclaminis; Cylindrocladium scoparium; Didymella bryoniae; Didymella lycopersici; Drechslera oryzae; Elsinoë fawcetti; Elsinoë veneta; Etysiphe* spp.; *Fulvia Alva; Cladosporiurm Fulvum; Fusarium culmorum; Fusarium grarninearum; Fusarium nivale; Fusarium oxysporum* spp.; *Fusarium roseurm; Fusariurm roseum* var.*sambucinum; Fusarium solani* f. sp. *pisi; Fusarium sulphureum; Fusicladiurm effusum; Gibberella fujikuroi; Gloeosporium* spp,; *Glomerella acutata; Guignardia citricarpa; Helminthosporium solani; Leveillula taurica; Monilinia* spp; *Mycosphaerella* spp.; *Neofabraea* spp.; *Oidiopsis taurica; Oidium begonia; Penicillium* spp.; *Pestalotiopsis longiseta; Pezicula alba; Phoma* spp.; *Podosphaera leucotricha; Rhyncosporium secalis; Rhizoctonia solani; Sclerotinia fructicola; Selerotinia homeocarpa; Sclerotinia sclerotorium; Sclerotium* spp.; *Septoria* spp.; *Sphaerotheca* spp.; *Sporobolormyces roseus; Stagonospora curtisii; Tapesia* spp.; *Trichoderma harzianum; Uncinula necator; Venturia* spp.; *Verticillium* spp.; *Podosphaera xanthii; Ustilago* spp.; *Alternaria* spp.; *Pyrenophora teres; Pyrenophora tritici-repentis; Pyricularia oryzae; Rhynchosporium secalis; Stemphylium vesicarium; Erwinia amylovora; Erwinia caratovora; Pseudomonas syringae* pv. *Tomato; Pseudomonas syringae* pv. *Syringae; Biumeria graminis; Biumeria graminis* f.sp. *trilici; Botryotinia fuckeliana; Blumeriella jaapii; Cladosporium caryigenum; Fusarium asiaticum; Mycovellosiella nattrassii; Puccinia graminis* spp.; *Magnapoorthe oryzae*; or *Metampsora* spp.

26. The method of claim 21, for the control of the following pathogens:

*Botrytis cinerea; Erwinia amylovora; Mycosphaerella graminicola; Colletotrichum graminicola; Fusarium graminearum; Fusarium oxysporum; Ustilago maydis; Blumeria graminis; Puccinia graminis* sp.; *Magnapoorthe oryzae; Melampsora* spp.; or *Rhizoctonia solani.*

* * * * *